(12) United States Patent
Brock

(10) Patent No.: US 7,297,142 B2
(45) Date of Patent: *Nov. 20, 2007

(54) INTERCHANGEABLE SURGICAL INSTRUMENT

(75) Inventor: David L. Brock, Natick, MA (US)

(73) Assignee: Hansen Medical, Inc., Mountain View, CA (US)

( * ) Notice: Subject to any disclaimer, the term of this patent is extended or adjusted under 35 U.S.C. 154(b) by 539 days.

This patent is subject to a terminal disclaimer.

(21) Appl. No.: 10/077,233

(22) Filed: Feb. 15, 2002

(65) Prior Publication Data

US 2002/0143319 A1 Oct. 3, 2002

Related U.S. Application Data

(60) Continuation-in-part of application No. 10/034,871, filed on Dec. 21, 2001, now Pat. No. 6,810,281, and a continuation-in-part of application No. 09/827,503, filed on Apr. 6, 2001, now Pat. No. 6,423,112, which is a continuation of application No. 09/746,853, filed on Dec. 21, 2000, now Pat. No. 6,692,485, which is a division of application No. 09/375,666, filed on Aug. 17, 1999, now Pat. No. 6,197,017, which is a continuation of application No. 09/028,550, filed on
(Continued)

(60) Provisional application No. 60/133,407, filed on May 10, 1999, provisional application No. 60/257,896, filed on Dec. 21, 2000, provisional application No. 60/195,264, filed on Apr. 7, 2000, provisional application No. 60/257,868, filed on Dec. 21, 2000, provisional application No. 60/257,867, filed on Dec. 21,
(Continued)

(51) Int. Cl.
*A61B 17/00* (2006.01)

(52) U.S. Cl. ............................... 606/1; 606/1; 606/130; 606/181; 600/102; 600/103; 600/117; 600/118; 348/65

(58) Field of Classification Search ................. 606/1, 606/130, 181, 146; 600/102–103, 117–118
See application file for complete search history.

(56) References Cited

U.S. PATENT DOCUMENTS 2,978,118 A 4/1961 Goertz et al.
3,923,166 A 12/1975 Fletcher et al.
(Continued)

FOREIGN PATENT DOCUMENTS

| EP | 0776738 A2 | 6/1997 |
| JP | 114000 | 7/1994 |
| WO | WO 93/14704 | 8/1993 |
| WO | WO98/25666 | 6/1998 |
| WO | WO00/60521 | 10/2000 |
| WO | WO 00/67640 | 11/2000 |
| WO | WO 02/074178 | 2/2002 |

OTHER PUBLICATIONS

Ikuta, et al., "Shape Memory Alloy Servo Actuator System With Electric Resistance Feedback And Application For Active Endoscope" 1988 IEEE, CH2555-1/88/0000/0427-430.
(Continued)

*Primary Examiner*—Vy Q. Bui
(74) *Attorney, Agent, or Firm*—Vista IP Law Group LLP

(57) ABSTRACT

A system and associated method for delivering to an internal body site a selected one of a plurality of instruments. An instrument storage chamber is providing having passages for separately accommodating a plurality of instruments. An outlet guide tube couples from the instrument storage chamber and receives a selected one of these instruments for delivery to an internal operative site. An indexing mechanism is provided associated with the chamber for causing relative displacement between the instruments and the outlet guide tube. An instrument driver displaces the registered instrument from the chamber into the outlet guide tube for delivery to the internal operative site.

32 Claims, 12 Drawing Sheets

Related U.S. Application Data

Feb. 24, 1998, now abandoned, application No. 10/077,233, which is a continuation-in-part of application No. PCT/US00/12553, filed on May 9, 2000, application No. 10/077,233, and a continuation-in-part of application No. 09/746,853, filed on Dec. 21, 2000, now Pat. No. 6,692,485, and a continuation-in-part of application No. PCT/US00/12553, filed on May 9, 2000, application No. 10/077,233, and a continuation-in-part of application No. 10/014,143, filed on Nov. 16, 2001, now abandoned, and a continuation-in-part of application No. 10/012,845, filed on Nov. 16, 2001, now Pat. No. 7,169,141, and a continuation-in-part of application No. 10/008,964, filed on Nov. 16, 2001, now abandoned, and a continuation-in-part of application No. 10/013,046, filed on Nov. 16, 2001, now abandoned, and a continuation-in-part of application No. 10/011,450, filed on Nov. 16, 2001, now abandoned, and a continuation-in-part of application No. 10/008,457, filed on Nov. 16, 2001, now Pat. No. 6,949,106, and a continuation-in-part of application No. 10/008,871, filed on Nov. 16, 2001, now Pat. No. 6,843,793, and a continuation-in-part of application No. 10/023,024, filed on Nov. 16, 2001, now abandoned, and a continuation-in-part of application No. 10/011,371, filed on Nov. 16, 2001, now Pat. No. 7,090,683, and a continuation-in-part of application No. 10/011,449, filed on Nov. 16, 2001, now abandoned, and a continuation-in-part of application No. 10/010,150, filed on Nov. 16, 2001, and a continuation-in-part of application No. 10/022,038, filed on Nov. 16, 2001, now abandoned, and a continuation-in-part of application No. 10/012,586, filed on Nov. 16, 2001.

Related U.S. Application Data 2000, provisional application No. 60/257,869, filed on Dec. 21, 2000, provisional application No. 60/257,816, filed on Dec. 21, 2000, provisional application No. 60/344,124, filed on Dec. 21, 2000, provisional application No. 60/332,287, filed on Nov. 21, 2001, provisional application No. 60/313,496, filed on Aug. 21, 2001, provisional application No. 60/313,497, filed on Aug. 21, 2001, provisional application No. 60/313,495, filed on Aug. 21, 2001, provisional application No. 60/279,087, filed on Mar. 27, 2001, provisional application No. 60/276,151, filed on Mar. 15, 2001, provisional application No. 60/276,217, filed on Mar. 15, 2001, provisional application No. 60/276,086, filed on Mar. 15, 2001, provisional application No. 60/276,152, filed on Mar. 15, 2001, provisional application No. 60/269,203, filed on Feb. 15, 2001.

U.S. PATENT DOCUMENTS

| Patent No. | | Date | Inventor(s) |
|---|---|---|---|
| 4,604,016 | A | 8/1986 | Joyce |
| 4,750,475 | A | 6/1988 | Yoshihashi |
| 4,853,874 | A | 8/1989 | Iwamoto et al. |
| 4,979,949 | A | 12/1990 | Matsen, III et al. |
| 5,078,140 | A | 1/1992 | Kwoh |
| 5,086,401 | A | 2/1992 | Glassman et al. |
| 5,154,717 | A | 10/1992 | Matsen, III et al. |
| 5,184,601 | A | 2/1993 | Putman |
| 5,217,003 | A | 6/1993 | Wilk |
| 5,236,432 | A | 8/1993 | Matsen, III et al. |
| 5,238,005 | A | 8/1993 | Imran |
| 5,299,288 | A | 3/1994 | Glassman et al. |
| 5,339,799 | A | 8/1994 | Kami et al. |
| 5,350,355 | A | 9/1994 | Sklar |
| 5,368,015 | A | 11/1994 | Wilk |
| 5,372,147 | A | 12/1994 | Lathrop, Jr. et al. |
| 5,382,885 | A | 1/1995 | Salcudean et al. |
| 5,397,323 | A | 3/1995 | Taylor et al. |
| 5,402,801 | A | 4/1995 | Taylor |
| 5,410,638 | A | 4/1995 | Colgate et al. |
| 5,417,210 | A | 5/1995 | Funda et al. |
| 5,441,505 | A | 8/1995 | Nakamura |
| 5,447,149 | A | 9/1995 | Kikawada et al. |
| 5,515,478 | A | 5/1996 | Wang |
| 5,524,180 | A | 6/1996 | Wang et al. |
| 5,540,649 | A | 7/1996 | Bonnell et al. |
| 5,553,198 | A | 9/1996 | Wang et al. |
| 5,572,999 | A | 11/1996 | Funda et al. |
| 5,618,294 | A | 4/1997 | Aust et al. |
| 5,624,398 | A | 4/1997 | Smith et al. |
| 5,626,595 | A | 5/1997 | Sklar et al. |
| 5,631,973 | A | 5/1997 | Green |
| 5,632,758 | A | 5/1997 | Sklar |
| 5,649,956 | A | 7/1997 | Jensen et al. |
| 5,657,429 | A | 8/1997 | Wang et al. |
| 5,754,741 | A | 5/1998 | Wang et al. |
| 5,762,458 | A | 6/1998 | Wang et al. |
| 5,784,542 | A | 7/1998 | Ohm et al. |
| 5,792,135 | A | 8/1998 | Madhani et al. |
| 5,800,333 | A | 9/1998 | Liprie |
| 5,800,423 | A | 9/1998 | Jensen |
| 5,807,377 | A | 9/1998 | Madhani et al. |
| 5,807,378 | A | 9/1998 | Jensen et al. |
| 5,808,665 | A * | 9/1998 | Green .......................... 348/65 |
| 5,810,880 | A | 9/1998 | Jensen et al. |
| 5,814,038 | A | 9/1998 | Jensen et al. |
| 5,815,640 | A | 9/1998 | Wang et al. |
| 5,817,084 | A | 10/1998 | Jensen |
| 5,821,920 | A | 10/1998 | Rosenberg et al. |
| 5,825,982 | A | 10/1998 | Wright et al. |
| 5,828,197 | A | 10/1998 | Martin et al. |
| 5,833,656 | A | 11/1998 | Smith et al. |
| 5,855,553 | A | 1/1999 | Tajima et al. |
| 5,855,583 | A | 1/1999 | Wang et al. |
| 5,876,325 | A | 3/1999 | Mizuno et al. |
| 5,878,193 | A | 3/1999 | Wang et al. |
| 5,907,664 | A | 5/1999 | Wang et al. |
| 5,931,832 | A | 8/1999 | Jensen |
| 5,954,692 | A | 9/1999 | Smith et al. |
| 5,954,731 | A * | 9/1999 | Yoon .......................... 606/144 |
| 5,971,976 | A | 10/1999 | Wang et al. |
| 5,976,122 | A | 11/1999 | Madhani et al. |
| 6,001,108 | A | 12/1999 | Wang et al. |
| 6,007,550 | A | 12/1999 | Wang et al. |
| 6,024,695 | A | 2/2000 | Taylor et al. |
| 6,036,636 | A | 3/2000 | Motoki et al. |
| 6,063,095 | A | 5/2000 | Wang et al. |
| 6,080,181 | A | 6/2000 | Jensen et al. |
| 6,096,004 | A | 8/2000 | Meglan et al. |
| 6,102,850 | A | 8/2000 | Wang et al. |
| 6,106,511 | A | 8/2000 | Jensen |
| 6,120,433 | A | 9/2000 | Mizuno et al. |
| 6,132,368 | A | 10/2000 | Cooper |
| 6,132,441 | A | 10/2000 | Grace |
| 6,197,017 | B1 | 3/2001 | Brock et al. |
| 6,206,903 | B1 | 3/2001 | Ramans |
| 6,223,100 | B1 | 4/2001 | Green |
| 6,231,565 | B1 | 5/2001 | Tovey et al. |
| 6,233,504 | B1 | 5/2001 | Das et al. |
| 6,246,200 | B1 | 6/2001 | Blumenkranz et al. |
| 6,290,675 | B1 | 9/2001 | Vujanic et al. |
| 6,301,526 | B1 | 10/2001 | Kim et al. |
| 6,309,397 | B1 | 10/2001 | Julian et al. |
| 6,312,435 | B1 | 11/2001 | Wallace et al. |
| 6,325,808 | B1 | 12/2001 | Bernard et al. |
| 6,331,181 | B1 | 12/2001 | Tierney et al. |
| 6,341,231 | B1 | 1/2002 | Ferre et al. |
| 6,346,072 | B1 | 2/2002 | Cooper |
| 6,364,888 | B1 | 4/2002 | Niemeyer et al. |
| 6,371,907 | B1 | 4/2002 | Hasegawa et al. |

| | | |
|---|---|---|
| 6,375,471 B1 | 4/2002 | Wendlandt et al. |
| 6,377,011 B1 | 4/2002 | Ben-Ur |
| 6,385,509 B2 | 5/2002 | Das et al. |
| 6,394,998 B1 | 5/2002 | Wallace et al. |
| 6,398,726 B1 | 6/2002 | Ramans et al. |
| 6,432,112 B2 | 8/2002 | Brock et al. |
| 6,436,107 B1 | 8/2002 | Wang et al. |
| 6,441,577 B2 | 8/2002 | Blumenkranz et al. |
| 6,451,027 B1 | 9/2002 | Cooper et al. |
| 6,459,926 B1 | 10/2002 | Nowlin et al. |
| 6,463,361 B1 | 10/2002 | Wang et al. |
| 6,468,265 B1 | 10/2002 | Evans et al. |
| 6,490,490 B1 | 12/2002 | Uchikubo et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,496,099 B2 | 12/2002 | Wang et al. |
| 6,517,565 B1 | 2/2003 | Whitman et al. |
| 6,522,906 B1 | 2/2003 | Salisbury, Jr. et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,594,552 B1 | 7/2003 | Nowlin et al. |
| 6,620,173 B2 | 9/2003 | Gerbi et al. |
| 6,645,196 B1 | 11/2003 | Nixon et al. |
| 6,676,684 B1 | 1/2004 | Morley et al. |
| 6,685,698 B2 | 2/2004 | Morley et al. |
| 6,692,485 B1 | 2/2004 | Brock et al. |
| 6,699,235 B2 | 3/2004 | Wallace et al. |
| 6,720,988 B1 | 4/2004 | Gere et al. |
| 6,726,675 B1 | 4/2004 | Beyar |
| 6,726,699 B1 | 4/2004 | Wright et al. |
| 6,728,599 B2 | 4/2004 | Wang et al. |
| 6,770,081 B1 | 8/2004 | Cooper et al. |
| 6,783,524 B2 | 8/2004 | Anderson et al. |
| 6,788,018 B1 | 9/2004 | Blumenkranz |
| 6,793,653 B2 | 9/2004 | Sanchez et al. |
| 6,799,065 B1 | 9/2004 | Niemeyer |
| 6,817,972 B2 | 11/2004 | Snow |
| 6,817,974 B2 | 11/2004 | Cooper et al. |
| 6,837,883 B2 | 1/2005 | Moll et al. |
| 6,840,938 B1 | 1/2005 | Morley et al. |
| 6,852,107 B2 | 2/2005 | Wang et al. |
| 6,860,877 B1 | 3/2005 | Sanchez et al. |
| 6,911,916 B1 | 6/2005 | Wang et al. |
| 6,936,001 B1 | 8/2005 | Snow |
| 6,951,535 B2 | 10/2005 | Ghodoussi et al. |
| 6,994,708 B2 | 2/2006 | Manzo |
| 7,025,064 B2 | 4/2006 | Wang et al. |
| 2005/0215983 A1 | 9/2005 | Brock |

OTHER PUBLICATIONS

M.W. Thring, "Robots And Telechirs: Manipulators With Memory; Remote Manipulators: Machine Limbs For the Handicapped", First published in 1983 by Ellis Horwood Limited.

Davies, BL, et al., "A Surgeon Robot for Prostatectomies," Center for Robotics, Imperial College of Science, *IEEE* (1991).

Kwoh, Y.S., et al., "A Robot with Improved Absolute Positioning Accuracy for CT Guided Sterotactic Brain Surgery," *IEEE Transactions on Biomedical Engineering*, 35(2) (1998).

Dohi, T., "Medical Application of Robotics Mechatronics," *International Biomedical Engineering Days*, (1992).

Sabatini, A.M., et al., "Force Feedback-Based Telemicromanipulation for Robot Surgery on Soft Tissue," *IEEE Engineering in Medicine & Biology Society*, (1989).

\* cited by examiner

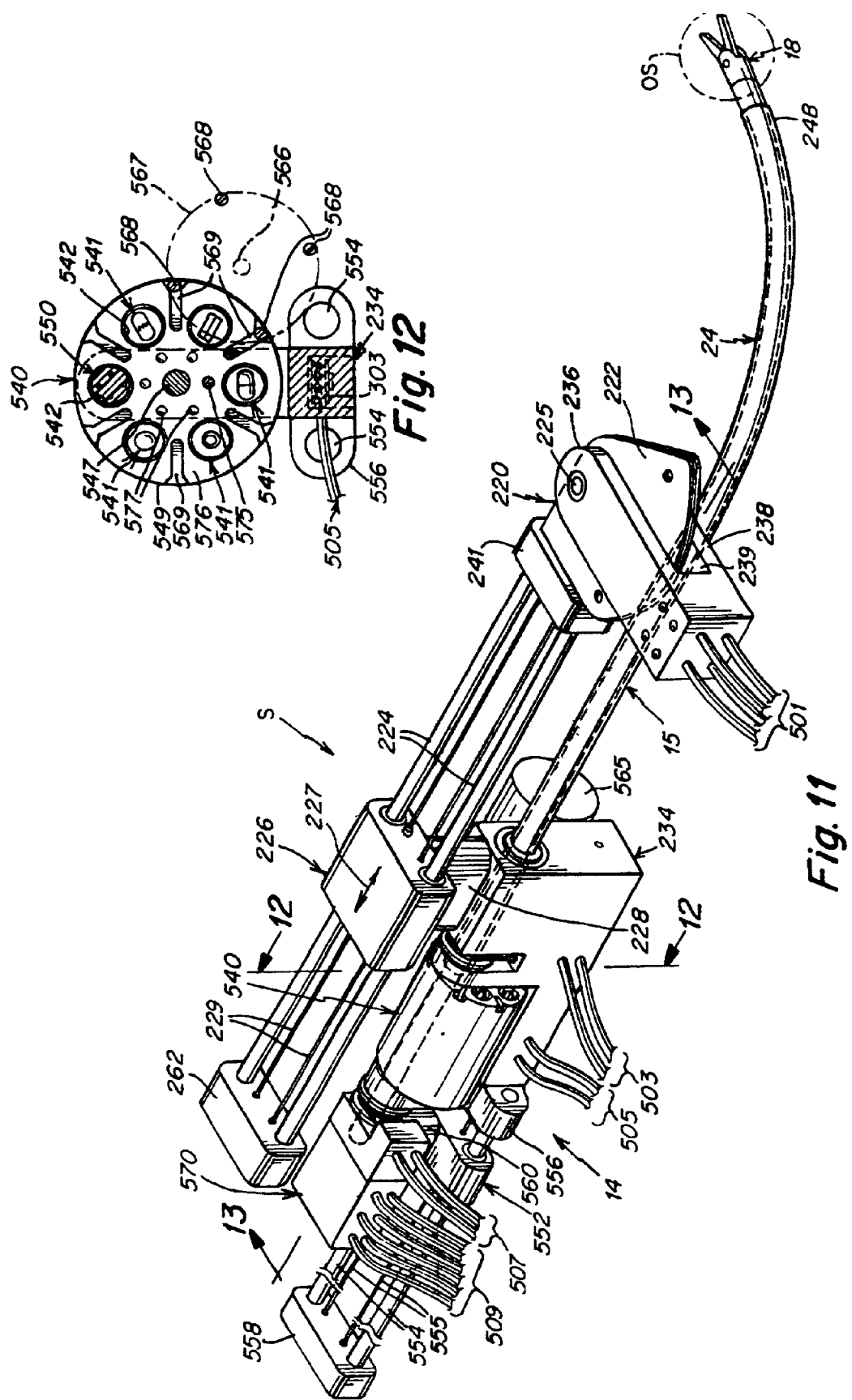

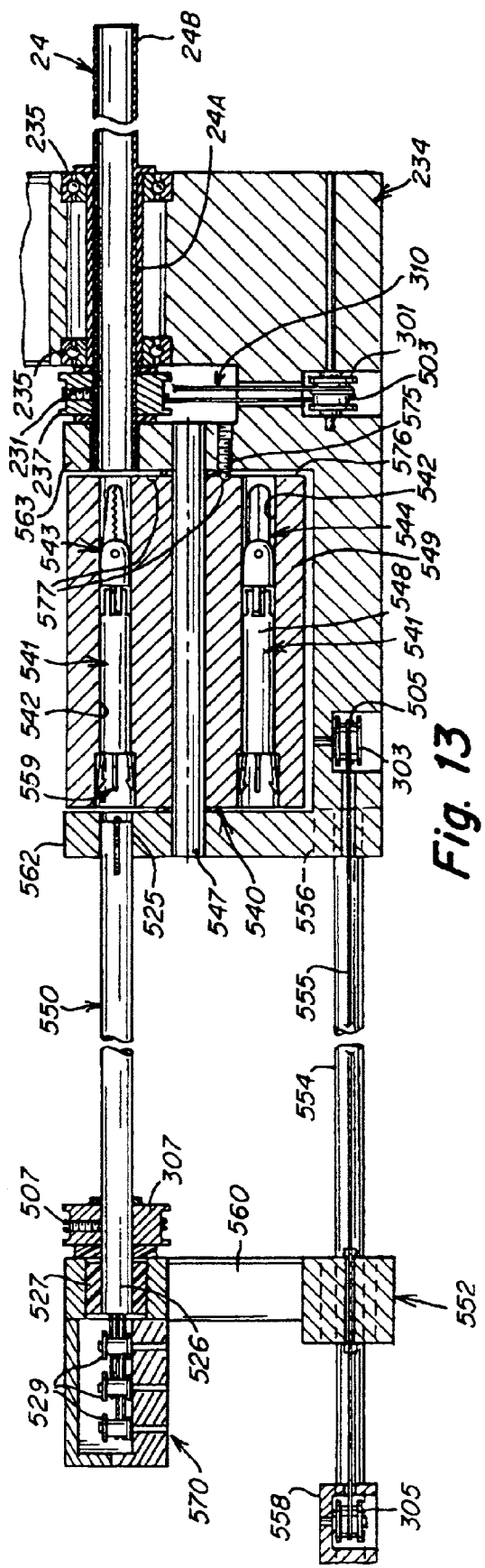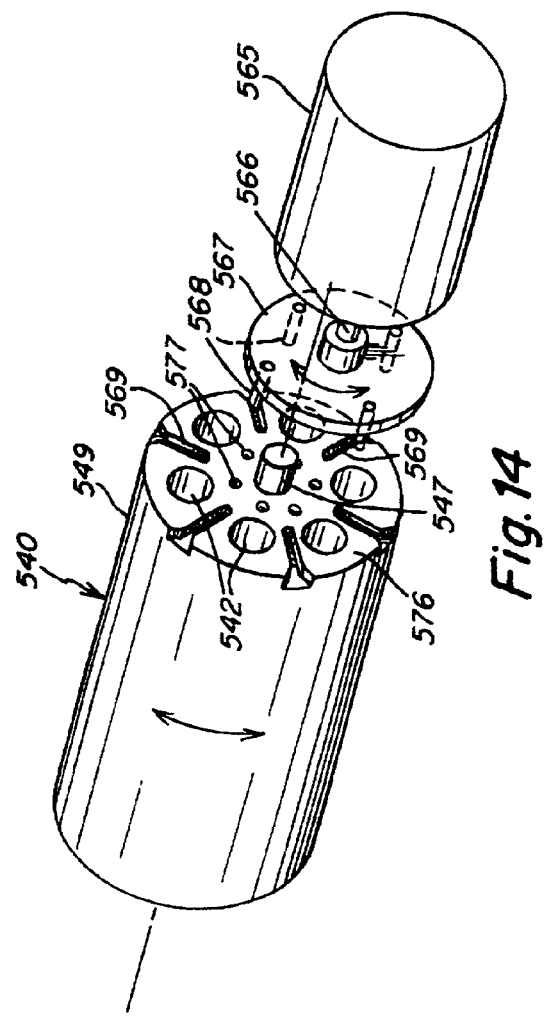
Fig. 13
Fig. 14

INTERCHANGEABLE SURGICAL INSTRUMENT

RELATED APPLICATIONS

This application is a continuation-in-part of and claims the benefit of priority from U.S. application Ser. No. 10/034,871, filed Dec. 21, 2001 now U.S. Pat. No. 6,810,281; U.S. application Ser. No. 09/827,503, filed Apr. 6, 2001 now U.S. Pat. No. 6,432,112, which is a continuation of U.S. application Ser. No. 09/746,853, filed Dec. 21, 2000 now U.S. Pat. No. 6,692,485, which is a divisional of U.S. application Ser. No. 09/375,666, now U.S. Pat. No. 6,197,017, filed Aug. 17, 1999, which is a continuation of U.S. application Ser. No. 09/028,550 filed Feb. 24, 1998, now abandoned. This application is also a continuation-in-part of and claims the benefit of priority from U.S. application Ser. No. 09/783,637, filed Feb. 14, 2001 now abandoned, which is a continuation of PCT/US00/12553 filed May 9, 2000, which claims the benefit of priority of U.S. provisional patent application Ser. No. 60/133,407, filed May 10, 1999, now abandoned. This application is also a continuation-in-part of and claims the benefit of priority from PCT/US01/11376 filed Apr. 6, 2001 which claims priority to U.S. application Ser. Nos. 09/746,853 filed Dec. 21, 2000 now U.S. Pat. No. 6,692,485 and Ser. No. 09/827,503 filed Apr. 6, 2001 now U.S. Pat. No. 6,432,112. This application is also a continuation-in-part of and claims the benefit of priority from U.S. application Ser. Nos. 09/746,853 filed Dec. 21, 2000 now U.S. Pat. No. 6,692,485 and Ser. No. 09/827,503 filed Apr. 6, 2001 now U.S. Pat. No. 6,432,211. This application is also a continuation-in-part of and claims the benefit of priority from U.S. application Ser. No. 09/827,643 filed Apr. 6, 2001 now U.S. Pat. No. 6,554,844 which claims priority to, inter alia, U.S. provisional application Ser. No. 60/257,869 filed Dec. 21, 2000 and U.S. provisional application Ser. No. 60/195,264 filed Apr. 7, 2000 and is also a continuation-in-part of PCT/US00/12553 filed May 9, 2000 from which U.S. application Ser. No. 09/783,637 filed Feb. 14, 2001 claims priority.

This application also claims the benefit of priority under 35 U.S.C. §§119 and 120 to U.S. Provisional Application Ser. No. 60/332,287 filed Nov. 21, 2001, U.S. Provisional Application Ser. No. 60/344,124, filed Dec. 21, 2001 U.S. Provisional Application Ser. No. 60/293,346 filed May 24, 2001, U.S. Provisional Application Ser. No. 60/279,087, filed Mar. 27, 2001, U.S. Provisional Application Ser. No. 60/313,496 filed Aug. 21, 2001, U.S. Provisional Application Ser. No. 60/313,497 filed Aug. 21, 2001, U.S. Provisional Application Ser. No. 60/313,495 filed Aug. 21, 2001, U.S. Provisional Application Ser. No. 60/269,203 filed Feb. 15, 2001, U.S. Provisional Application Ser. No. 60/269,200 filed Feb. 15, 2001, U.S. Provisional Application Ser. No. 60/276,151 filed Mar. 15, 2001, U.S. Provisional Application Ser. No. 60/276,217 filed Mar. 15, 2001, U.S. Provisional Application Ser. No. 60/276,086 filed Mar. 15, 2001, U.S. Provisional Application Ser. No. 60/276,152 filed Mar. 15, 2001, U.S. Provisional Application Ser. No. 60/257,816 filed Dec. 21, 2000, U.S. Provisional Application Ser. No. 60/257,868 filed Dec. 21, 2000, U.S. Provisional Application Ser. No. 60/257,867 filed Dec. 21, 2000, U.S. Provisional Application Ser. No. 60/257,869 filed Dec. 21, 2000.

This application further is a continuation-in-part of and claims the benefit of priority from the following U.S. patent applications all filed on Nov. 16, 2001 and identified as U.S. Ser. No. 10/014,143 now abandoned; U.S. Ser. No. 10/012,845 now U.S. Pat. No. 7,169,141; U.S. Ser. No. 10/008,964 now abandoned; U.S. Ser. No. 10/013,046 now abandoned; U.S. Ser. No. 10/011,450 now abandoned; U.S. Ser. No. 10/008,457 now U.S. Pat. No. 6,949,106; U.S. Ser. No. 10/008,871 now U.S. Pat. No. 6,843,793; U.S. Ser. No. 10/023,024 now abandoned; U.S. Ser. No. 10/011,371 now U.S. Pat. No. 7,090,683; U.S. Ser. No. 10/011,449 now abandoned; U.S. Ser. No. 10/010,150; U.S. Ser. No. 10/022,038 now abandoned; and U.S. Ser. No. 10/012,586.

The disclosures of all of the foregoing applications and U.S. Pat. No. 6,197,017 are all incorporated herein by reference in their entirety.

BACKGROUND OF THE INVENTION

The present invention relates in general to medical instrumentation. More particularly, the present invention relates to a surgical instrumentation system that enables the interchange of any one of a number of different surgical instruments at an operative site.

In open surgery a surgeon uses a variety of different surgical implements with the total number that are used being a function of the particular operation being performed. For the most part these instruments or implements are hand held devices directly held and manipulated by the surgeon through the open incision. Typical surgical instruments include forceps, needle drivers, scissors, scalpels, etc. A number of different instruments or implements may be used during an operation depending upon the complexity of the medical procedure being performed, and even a greater number of instrument exchanges occur. Thus, a great deal of time may be spent during the surgery simply in exchanging between different types of instruments.

In minimally invasive surgery (MIS) there is likewise a requirement, depending upon the particular surgical procedure, to exchange instruments or implements during a medical procedure. The primary difference in minimally invasive surgery is that the incision or incisions are relatively small, typically 5 mm to 10 mm in diameter, in comparison to open surgery. Also, in current MIS instrumentation, such instruments as forceps, scissors, etc., are inserted into the body at the end of long slender push rods actuated by the surgeon from outside the patient. Due to the size and increased complexity of these instruments it may be even more difficult to carry out an exchange due to the need to extract and re-insert through a relatively small incision.

Both open and MIS procedures involve control of the instrument directly by the human hand. In the case of open surgery, of course, the surgeon directly holds and manipulates the instrument, while in MIS the operable tool (scalpel, scissors, etc.) is controlled by hand, but through some type of mechanical transmission that intercouples from outside the patient to an internal operative site.

In more recent years computer control of instrumentation systems has come into being, typically referred to as robotic surgical systems, in which a surgeon controls an instrument carrying an end effector from a remote site, and through an electronic controller or the like. These robotic systems do provide an improvement in the dexterity with which medical procedures can be performed. However, even in these more advanced systems there is still a need to manually exchange instruments during a procedure.

Accordingly, it is an objective of the present invention to provide a system and associated method for the ready exchange or interchange between a plurality of different instruments at an operative site, whether it be in connection with open, MIS, robotic, or other types of surgical systems, apparatus, or procedures.

BRIEF SUMMARY OF THE INVENTION

The present invention is directed to a system, apparatus, or method for enabling the exchange or interchange between one of several different instruments or implements, so that these different instruments or implements can be readily delivered to an operative or target site within a patient for performing a medical or surgical procedure. The present invention carries out this exchange or interchange without the usual manual withdrawal and insertion that is typical of prior art systems, and can be said to perform this interchange or exchange essentially automatically, with little or no manual intervention. The principles of the present invention are intended to apply to any instruments or implements, whether for open, MIS, or robotic surgery uses. The tool or end effector of the instrument may be of any type including, but not limited to, articulated and non-articulated types.

In accordance with one aspect of the present invention there is provided an interchangeable instrument apparatus that includes a plurality of separate instrument members each capable of assisting in a different phase of a medical procedure to be performed at an operative site within the anatomy. An instrument storage chamber releasably receives the plurality of instrument members. The instrument members are accommodated in separate storage locations within the instrument storage chamber. An instrument driver is constructed and arranged for cooperative positioning relative to the instrument storage chamber, for selective alignment with one of the instrument members at a time, and for displacing or driving the aligned instrument member from the instrument storage chamber toward the operative site. At least one of the instrument driver and instrument storage chamber are positionally controllable so as to provide relative displacement therebetween so as to selectively align the instrument driver with another of the instrument members.

In accordance with another aspect of the present invention there is provided a surgical instrument apparatus that comprises an instrument member that includes two sections including a work section that supports at its distal end a tool used in performing a medical procedure at an operative site within the anatomy, and a driver section that is releasably engageable with the work section. The apparatus also includes a guide member for receiving the work section and the driver section, and for directing, upon engagement of said driver section with said work section, the delivery of the tool to the operative site. The driver section, in an inoperative position thereof, is disengaged from the work section, and in an operative position thereof, is engageable with the work section to direct the work section, via the guide member, to the operative site, and further is engageable with the work section to enable operative coupling to the tool for actuation of the tool from a remote drive unit.

In accordance with still another aspect of the present invention there is provided a method of delivering, to an internal operative site, a selected one of a plurality of instruments. The method comprising the steps of; storing a plurality of separate instruments in a storage chamber with each instrument capable of assisting in a different phase of a medical procedure to be performed at the operative site, and providing an instrument driver constructed and arranged for;
  cooperative positioning relative to the instrument storage chamber,
  selective alignment with one of the instruments at a time, and
  displacing the aligned instrument from the instrument storage chamber.

At least one of the instrument driver and instrument storage chamber are positionally controlled so as to provide relative displacement therebetween, and so as to selectively align the instrument driver with another one of the instrument members In accordance with another aspect of the present invention there is provided a storage chamber that supports a plurality of separately arranged instruments, and further includes inlet and outlet ports. The outlet port is arranged in alignment with the target or operative site where the instrument is to be delivered. The instrument carries at its distal end a work implement(tool). An instrument driver is in alignment with the inlet port, and is adapted to engage a registered instrument disposed in the storage chamber, so as to deliver the selected instrument, via the outlet port, to the target or operative site. The instrument driver, in addition to engagement with the instrument, also operatively couples with and enables operation of the work implement of the instrument. The storage chamber is selectively operable, upon command, to permit different instruments to align between the inlet and outlet ports.

In accordance with another aspect of the present invention there is provided a surgical instrument apparatus that includes an instrument member having a work section that supports at its distal end a tool used in performing a medical procedure at an operative site within the anatomy, and a driver section that is releasably engageable with the work section. A guide member receives the work section and the drive section, and is for directing, upon engagement of the driver section with the work section, the delivery of the tool to the operative site. The driver section, in an inoperative position thereof, is disengaged from the work section, and in an operative position thereof, is engageable with the work section to direct the work section, via the guide member, to the operative site, and is further engageable with the work section to enable operative coupling to the tool for actuation of the tool from a remote drive unit. The apparatus also preferably includes an interface or coupling section between the work and driver sections for selectively and releasably intercoupling therebetween.

The present invention is also directed to an interchangeable medical instrument system that includes an instrument storage retainer that supports a plurality of separately arranged instruments, and further includes inlet and outlet ports, the outlet port arranged in alignment with a target or operative site where the instrument is to be delivered for performing a medical procedure. A work implement is supported at the distal end of each instrument. An instrument transporter is in alignment with the inlet port, and adapted to engage a registered instrument disposed in the storage retainer, so as to deliver the selected instrument, via the outlet port to the target or operative site. The instrument transporter, in addition to engagement with the instrument, also operatively couples with and enables operation of the work implement of the instrument The retainer is selectively operable, upon command, to permit different instruments to align between the inlet and outlet ports.

The present invention is also directed to an interchangeable instrument system that includes an instrument retainer having multiple storage location for receiving a plurality of instruments disposed separately in the respective storage locations, and an instrument driver constructed and arranged for cooperative positioning relative to the instrument retainer, for selective alignment with one of the instruments at a time, and for displacing the aligned instrument from the instrument retainer and toward the operative site. An indexing mechanism controls the position of the instrument retainer so as to selectively align different instruments with the instrument driver. An actuation member is disposed at a user interface for controlling the indexing mechanism.

Another aspect of the present invention is an interchangeable instrument system that includes a plurality of medical instruments, an instrument retainer for releasably holding the plurality of instruments, and an instrument transporter associated with the instrument retainer, for selective alignment with one of the instruments at a time, and for displacing the aligned instrument from the instrument retainer toward an operative site in a subject. Either the instrument retainer or instrument transporter may be positionally controllable so as to provide relative displacement therebetween so as to selectively align the instrument transporter with another instrument. The instrument retainer may comprise a rotating chamber having a plurality of passages therein. Alternatively, the instrument retainer may comprise a linear chamber for receiving the instruments. The transporter may be positioned in parallel to the linear chamber, and a selected instrument is moved transversely out of the chamber for alignment with the instrument transporter.

In another aspect of the invention there is provided a remotely controllable medical apparatus comprising: a remote user interface manually manipulable by a user for sending operation command signals to a signal processor, the signal processor processing the command signals and sending processed signals to a drive mechanism; an instrument exchange mechanism mechanically intercoupled to the drive mechanism; the instrument exchange mechanism comprising a shaft and an instrument delivery mechanism containing two or more selected instruments; the shaft having a lumen which readily receives the selected instruments for insertion and withdrawal from the lumen; the instrument delivery mechanism being drivably movable to align a selected instrument with the lumen of the shaft for insertion and withdrawal to and from the lumen, the instrument delivery mechanism being remotely drivable via the user interface to insert and withdraw selected instruments.

In another aspect of the invention there is provided a remotely controllable medical apparatus comprising: a remote user interface manually manipulable by a user for sending operation command signals to a signal processor, the signal processor processing the command signals and sending processed signals to a drive mechanism; an instrument exchange mechanism mechanically intercoupled to the drive mechanism; the instrument exchange mechanism comprising a shaft and an instrument delivery mechanism containing two or more selected instruments; the shaft having a lumen which readily receives the selected instruments for insertion and withdrawal from the instrument delivery mechanism; an instrument drive mechanism mechanically intercoupled to the drive mechanism and readily mechanically couplable to and decouplable from an instrument; the instrument drive mechanism being remotely drivable via the user interface to operably couple to and drive an instrument.

BRIEF DESCRIPTION OF THE DRAWINGS

These and other features of the present invention are described in greater detail in the following detailed description, taken in conjunction with the accompanying drawings, in which:

FIG. 11 is a perspective view at the slave station of the system of FIG. 10 illustrating the interchangeable instrument concepts;

FIG. 12 is a cross-sectional view through the storage chamber and as taken along line 12-12 of FIG. 11;

FIG. 13 is a longitudinal cross-sectional view, as taken along line 13-13 of FIG. 11;

FIG. 14 is a perspective schematic view of the indexing mechanism used in the embodiment illustrated in FIGS. 10-13;

DETAILED DESCRIPTION

Figure 1:
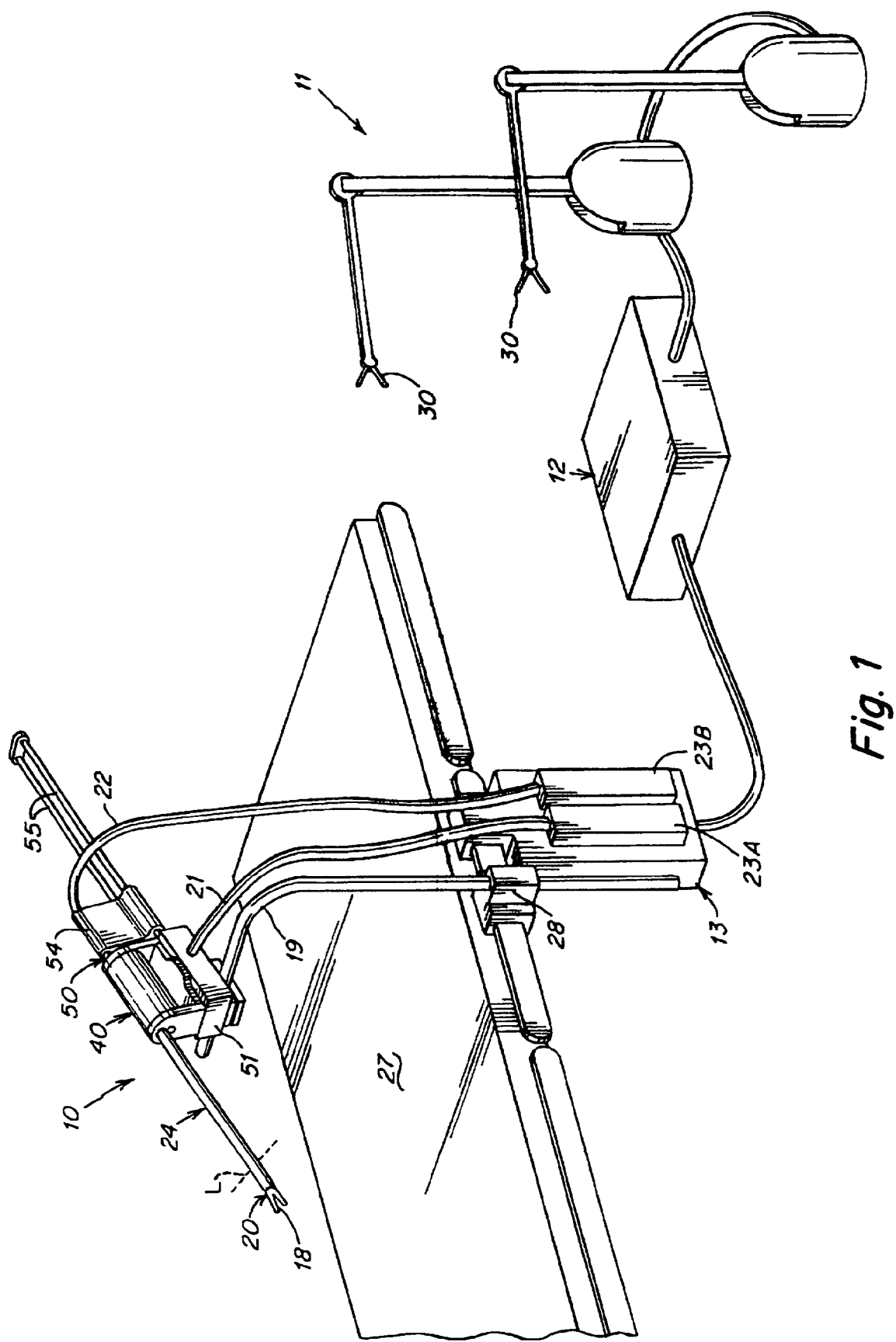
FIG. 1 is a perspective view of one embodiment of a robotic surgical system in which the interchangeable instrument principles of the present invention are applied.

In this detailed description there is described an apparatus for enabling the interchange, at an operative site, between different types of surgical instruments and in an automated fashion. In this way a substitution of one instrument for another can be readily accomplished, without manually withdrawing one instrument followed by manual insertion of another instrument. Further, with this apparatus, and the associated use of a guide tube, or the like, for receiving and guiding the instrument, the interchange can be carried out quickly and safely, thus enabling medical procedures to be performed in a far shorter period of time. The guide tube preferably extends to the operative site OS (see FIG. 7) so that the instrument can transition safely thereto. Also, the guide tube preferably remains at the operative site even as the instruments are exchanged in the guide tube, so as to avoid any tissue or organ damage during an instrument exchange. The operative site may be defined as the general area in close proximity to where movement of the tool occurs in performing a surgical procedure, usually in the viewing area of the endoscope and away from the incision.

In this description the instrument interchange principles are illustrated in association with two separate surgical systems, both of which are robotic systems, sometimes also referred to as telerobotic systems. However, the principles of this invention also apply to other surgical instrumentation, such as used in minimally invasive surgery (MIS), where a number of instrument exchanges are typical in performing a medical or surgical procedure.

It is assumed, by way of example, that the systems disclosed herein are for use in laparoscopic surgery. Thus, one system is disclosed in FIGS. 1 through 8A and 8B, while a second system is disclosed in FIGS. 10-14. A variation of the first system is illustrated in FIG. 9. It is noted that in FIG. 9, the instrument-to-driver registration is accomplished with a linear arrangement, while in the other versions described herein a rotating arrangement is employed, all to be described in further detail later. Also, in the embodiments described herein the driver has only linear translation while the instrument storage chamber rotates (FIGS. 1 and 10) or slides (FIG. 9). In an alternate embodiment the driver may rotate or otherwise move to different registration positions, as the instrument storage chamber remains stationary, as long as there is relative motion between the instrument driver and instrument storage chamber.

Before reference is made to the detailed embodiments described herein, consideration is given to co-pending applications that are hereby incorporated by reference herein in their entirety, and that describe in further detail aspects of the several components that make up the overall robotic surgery system. In connection with descriptions set forth herein reference is made to the applications set forth in the related application part of this application as well as to pending U.S. application Ser. No. 09/783,637 filed Feb. 14, 2001; U.S. application Ser. No. 10/014,143 filed Nov. 11, 2001; as well as issued U.S. Pat. No. 6,197,017.

Figure 5:
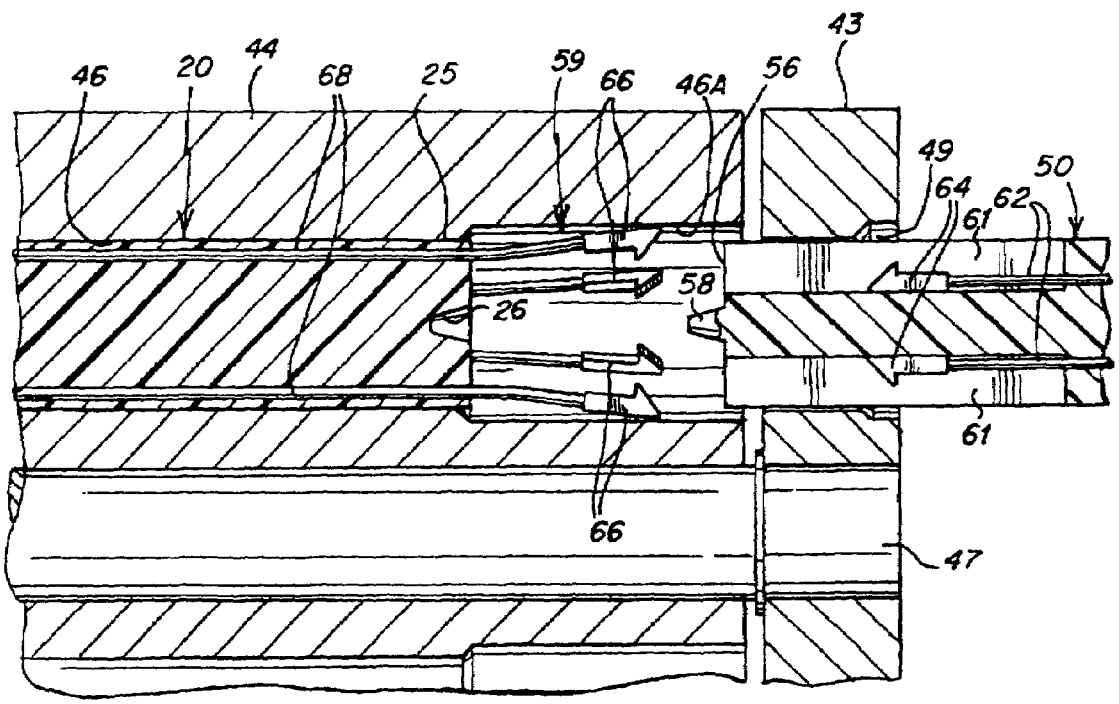
FIG. 5 is a partial cross-sectional view showing further details of the driver and instrument in this first embodiment.
Figure 6:
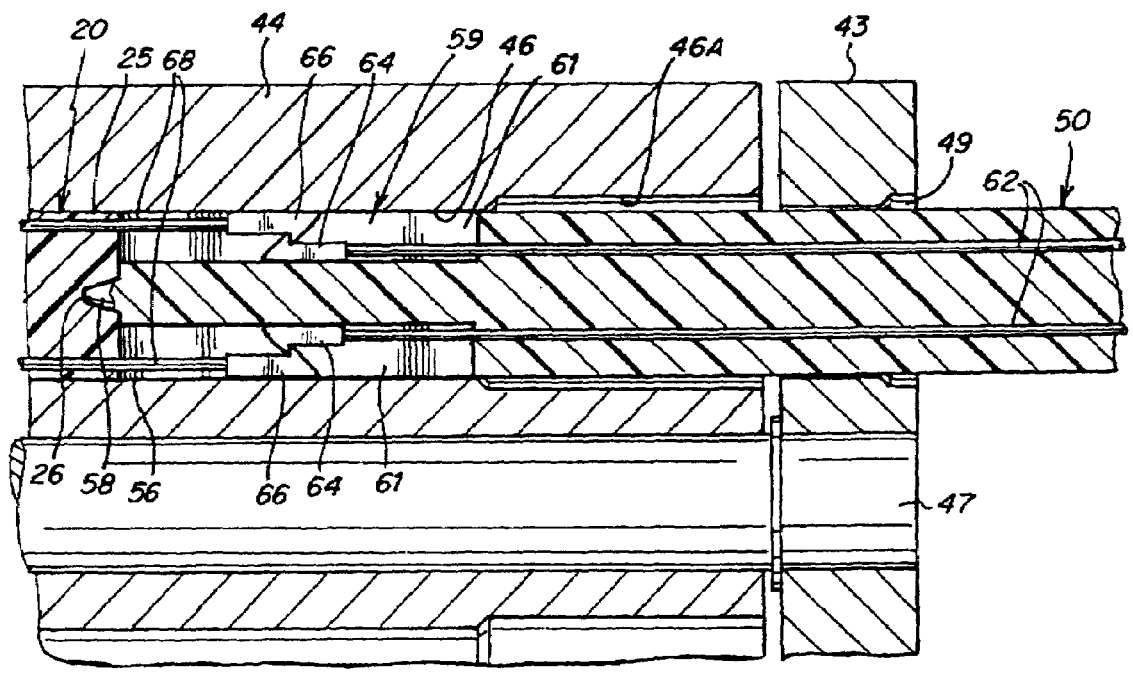
FIG. 6 is a further cross-sectional view similar to that illustrated in FIG. 5 but showing the driver and instrument in an interlocked position.
Figure 7:
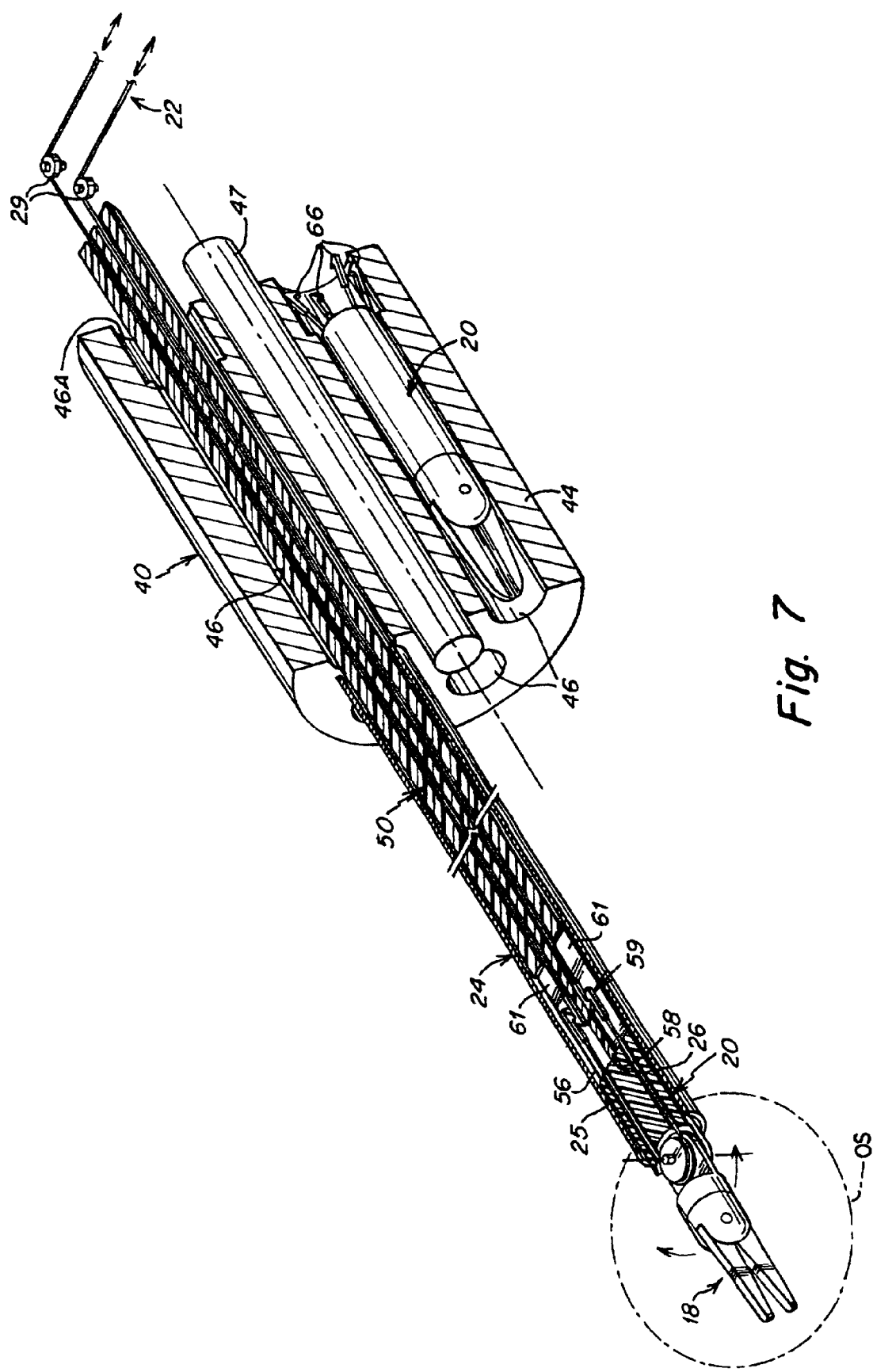
FIG. 7 is a schematic cross-sectional perspective view that illustrates details of the instrument of the present invention.

The first embodiment of the invention is illustrated in FIGS. 1-8. FIG. 1 shows a surgical instrument system 10 that performs surgical procedures. The system may be used to perform minimally invasive procedures. The system may also be used to perform open or endoscopic surgical procedures. The system 10 includes a surgeon interface 11, computation system 12, and drive unit 13. The system controls the instrument so as to position the end effector (tool) 18 of the instrument 20 at the very distal end of and extending through the outlet guide tube 24. During use, a surgeon may manipulate the handles 30 of the surgeon interface 11, to effect desired motion of the end effector 18 within the patient, at the operative site which is schematically illustrated in FIG. 7. The movement of a handle 30 is interpreted by the computation system 12 to control the movement of the end effector (tool) 18.

The system may also include an endoscope with a camera to remotely view the operative site. The camera may be mounted on the distal end of the instrument, or may be positioned away from the site to provide additional perspective on the surgical operation. In certain situations, it may be desirable to provide the endoscope through an opening other than the one used by the instrument.

The entire assembly illustrated in FIG. 1 is shown supported over the surgical table 27, and in a position so that the guide tube 24 can be inserted through an incision in the patient and directed to the operative site of the patient. The incision is represented in FIG. 1 by the dashed line L. The surgical instrument system 10 of the present invention is preferably mounted on rigid post 19 which may be movably affixed to the surgical table 27, at bracket 28.

The surgical system 10 includes two mechanical cable-in-conduit bundles 21 and 22. These cable bundles 21 and 22 terminate at one end at the two connection modules(couplers) 23A and 23B, which removably attach to the drive unit 13. The drive unit 13 is preferably located outside the sterile field, although it may be draped with a sterile barrier so that it may be operated within the sterile field. The other end of the bundles terminate at the surgical system 10. These terminations are shown in further detail in the description of the second embodiment that is described later. Basically cables in the bundle 21 may control; the indexing for controlled rotation of the instrument storage chamber 40; rotation of the guide tube 24; as well as motion of the carriage 54 for control of the linear translation of the driver 50. On the other hand the bundle 22 may control, for example, rotation of the instrument within the guide tube 24, as well as actuation of the tool 18. The instrument storage chamber is also referred to herein as an instrument retainer.

FIG. 1 also shows the instrument storage chamber 40 that is illustrated as supported over the base piece 51, which, in turn, is supported from the rigid post 19. The cable bundle 21 couples to the base piece 51 and controls motion of the instrument storage chamber 40, as well as the driver 50. The guide tube 24 is supported at the outlet port side of the instrument storage chamber 40, and is controlled for rotation relative to the instrument storage chamber 40. Rotation of the guide tube 24 provides a corresponding rotation of the instrument and tool. The instrument storage chamber 40 has at its inlet side a port for receiving the driver 50, and for permitting engagement of the driver with the one of the instruments in the instrument storage chamber 40 that is in registration with the driver 50. The driver 50 is supported from the carriage 54 which transitions on rails 55, and is controlled from cable bundle 22. The driver may also be referred to herein as an instrument transporter.

In accordance with the setup of the system of FIG. 1, the guide tube 24 of the surgical instrument system 10 is inserted into the patient usually through an incision. Usually, a cannula is positioned in the incision, is maintained in position and receives the guide tube 24. This incision is illustrated in FIG. 1 by the dashed line L. The system is then mounted to the rigid post 19. The cable bundles 21 and 22 are then coupled to the drive unit 13. The connection modules or couplers 23A and 23B at the end of respective cable bundles 21 and 22 are then engaged into the drive unit 13. The system is then ready for use and control from the master station side at surgeon interface 11. For further details of the entire slave side of the system, including the drive unit, detachability at the drive unit, the cabling and cable couplers, refer to U.S. Ser. Nos. 09/783,637; and 10/014,143, previously mentioned.

Now, reference is made, not only to FIG. 1 but also to FIGS. 2 through 6 that illustrate further details depicting the interchangeable instrument concepts of the present invention. FIG. 7 illustrates schematically a cabling scheme that may be used in the instrument. FIG. 9 illustrates an alterative to the revolving chamber construction, in the form of a linearly translatable housing or chamber arrangement.

The revolving instrument storage chamber 40 includes a base 42, opposite end walls 43 and a cylindrical chamber or magazine 44. In the embodiment illustrated herein, chamber 44 has six elongated passages 46 each for receiving an instrument. The chamber 44 is supported by a centrally disposed support rod 47, such as illustrated in FIG. 5. The support rod 47 may be supported in bearings (not shown) at the opposite end walls 43. The instrument storage chamber 40 has its rotation controlled at base piece 51 (see FIG. 1) so that when an operator at interface 11 wants to change instruments, a command can be sent from the master to the slave side to rotate the magazine 44 so that a different instrument is in alignment with the driver 50. Of course, this exchange only occurs when the driver has been withdrawn to its rest (disengaged) position. Specific sequences of the interchange action are described later. The command that is sent may be initiated by any one of several means, some of which are described in some detail later.

Figure 2:
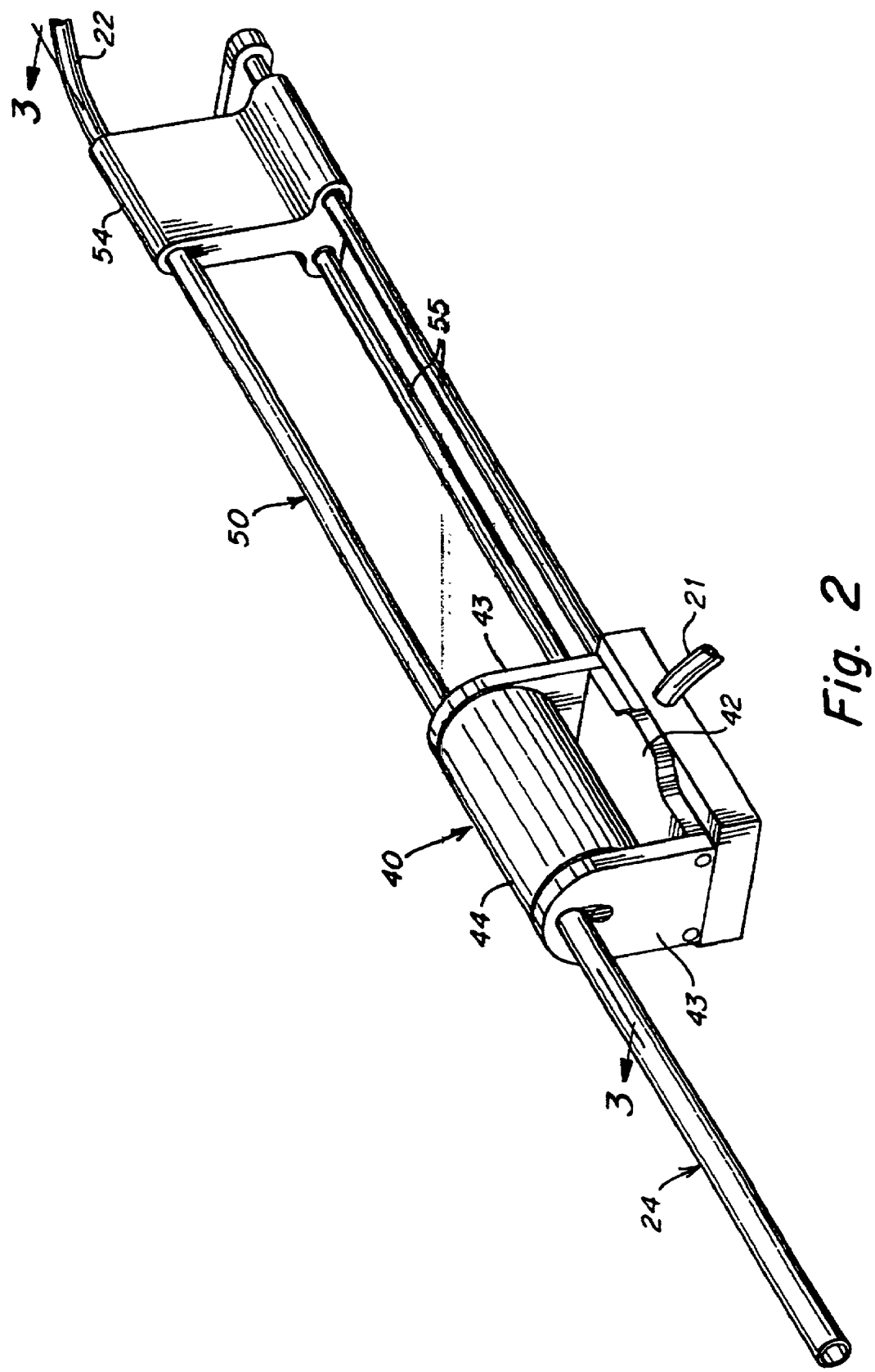
FIG. 2 is a perspective view showing a portion of the system of FIG. 1, particularly the storage chamber and the driving mechanism.
Figure 3:
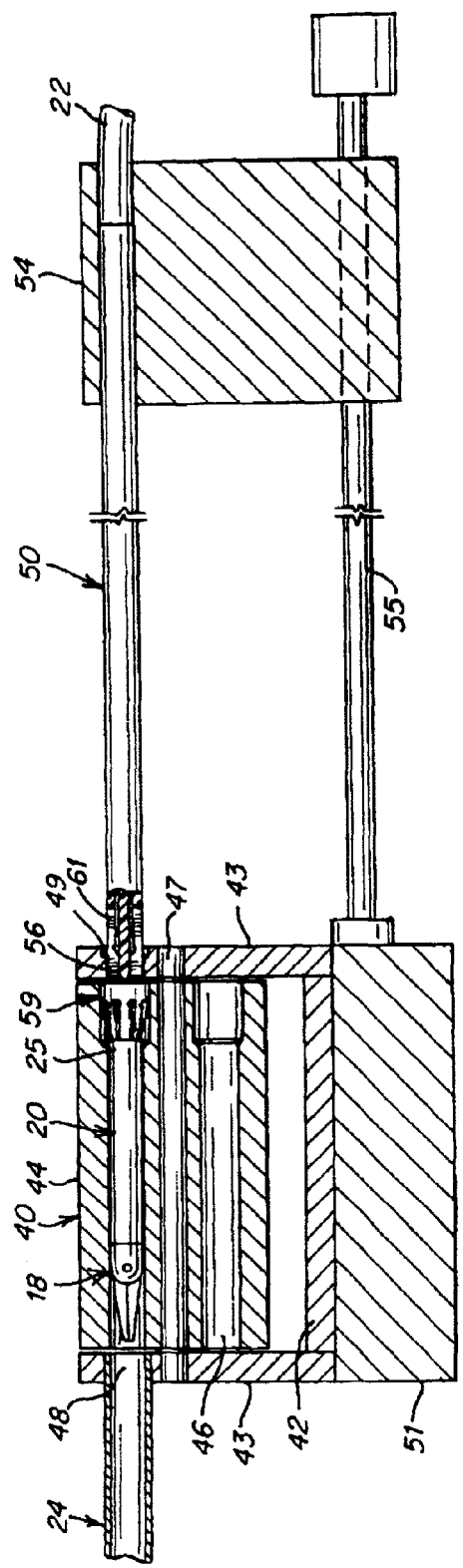
FIG. 3 is a cross-sectional view illustrating the storage chamber, the driver and the associated positioning of components, and as taken along line 3-3 of FIG. 2.

FIGS. 2 and 3 also illustrate the outlet guide tube 24. The tube 24 is secured to one of the end walls 43 and is essentially fixed in axial position relative to that end wall 43 of the rotating instrument storage chamber 40, but is capable of rotation on its own axis, and relative to the chamber 40. Details of this rotational support are described further in connection with the second embodiment described in FIGS. 10-14. The end walls 43 supporting the magazine 44 are fixed to the base 42, which is supported over the base piece 51 which, in turn, is fixed to the rigid post 19. Thus, in this particular embodiment the instrument storage chamber 40 rotates but does not have any significant linear movement toward or away from the operative site. Thus, in this first embodiment the instrument control has a somewhat limited number of degrees-of-freedom. The degrees-of-freedom can be increased by providing the guide tube with a curved distal end, like that illustrated in the second embodiment of the invention in FIGS. 10-14.

FIGS. 1 through 6 also illustrates the instrument driver 50. The instrument driver 50 is adapted to enter an end inlet port 49 in the wall 43 of the rotating chamber 40. In this regard, refer to FIG. 3 for the inlet port 49. Also, as discussed previously in connection with FIG. 1, in the base piece 51 there is an indexing mechanism that controls the rotation of the rotating storage chamber 44 so that different ones of the passages 46 are adapted to be aligned with the input driver port 49. This registration control may be carried out using a detent mechanism so that the proper instrument is aligned and selected from the chamber by the instrument driver 50. Refer to FIG. 2 and the cable bundle 21 that interconnects with the chamber 44 for selective and registered rotation thereof. Also, refer to FIG. 14 for an example of an indexing mechanism.

In a similar manner, at the opposite end wall 43 of the chamber 40, there is provided an outlet port 48, such as illustrated in FIG. 3, and that aligns with the outlet guide tube 24. Also, in FIGS. 2 and 3 there is illustrated the carriage 54 that carries the instrument driver 50 and that transitions along the support rails 55 to enable the driver to selectively engage with and drive the instrument forward through the guide tube 24 and toward the operative site.

FIG. 3 illustrates a cross-sectional view of one embodiment of the interchangeable instrument apparatus of the present invention. An instrument 20 with its end effector (tool) 18 is illustrated disposed in one of the elongated chambers 46 of the rotating chamber 44. In practice, each of the other passages 46 can contain other types of instruments, with a variety of different tool or end effectors. For the sake of clarity, only one of the instruments is illustrated in FIG. 3, it being understood that up to six other instruments of different types may be disposed in other ones of the elongated passages 46. Also, the magazine 44 may be constructed with fewer or more instrument-receiving passages. FIG. 3 also illustrates the driver 50 in a position where the end 56 thereof is positioned just entering the inlet port 49 with the end 56 about to engage the end 25 of the instrument 20. The position of the instrument driver 50 is considered as a "rest position" when the end 57 is disposed in wall 43, but has not yet entered the magazine 44 so that the magazine 44 is free to rotate. To interlock and align the driver and the instrument, there is provided a post 58 (see FIG. 5) on the driver 50 and an accommodating recess 26 (see FIG. 5) in the instrument end 25.

As mentioned previously, there are mechanical cables extending in bundles 21 and 22 illustrated in FIG. 1. The cables in bundle 22, in particular, couple by way of pulleys and then extend the length of the driver 50 to the instrument 20. The cabling and control pulley arrangements are disclosed in further detail in the second embodiment as shown in FIGS. 10-14. This cabling is for operating the end effector 18 illustrated in FIG. 1. To provide continuity of this mechanical control cabling, both the instrument driver as well as the instrument carry interconnecting cable connections. These are illustrated clearly in FIGS. 4 through 6. Also refer to the schematic perspective view of FIG. 7 showing the manner in which the cables couple about pulleys 29 and extend through the driver to intercouple with cabling of the instrument 20. These cable connections between the driver and instrument may also be considered as defining a coupling section or coupling interface 59 where the driver and instrument are releasably engageable. One may also consider the driver and instrument, such as illustrated in FIGS. 1-6, as collectively being an instrument member including a work section (instrument 20 and tool 18), and a driver section (driver 50).

Figure 4:
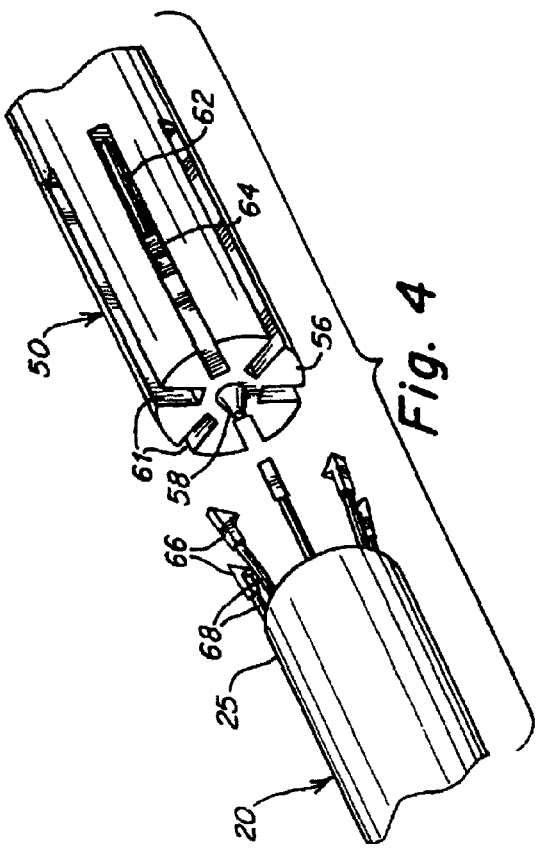
FIG. 4 is a perspective view showing some further detail of the instrument in this first embodiment.

The instrument driver 50 has passages 61 (see FIG. 4) for receiving a cable 62 (see FIGS. 4, 5 and 6). As illustrated in FIGS. 4, 5 and 6 the end of cable 62 terminates in a hook 64. The hook 64 is adapted to engage with a similar-configuration hook 66 at the end of cable 68 as illustrated in FIG. 6. FIG. 4 illustrates a series of slots or passages 61, which in the illustrated embodiment comprise six such slots 61. Each of these slots receives a cable 62 with its end hook 64.

Referring further to FIG. 4, this illustrates the end 25 of the instrument 20. Also illustrated are the elongated slots 61 in the driver(transporter) 50. FIG. 4 illustrates the cables 68 and their associated hooks 66 associated with the instrument 20. Also shown is the cable 62 with its hook 64 disposed in slot 61.

FIG. 5 illustrates the end 56 of the instrument driver 50 as the driver 50 is transitioning through the port 49 for engagement with the instrument 20. The driver 50 has not yet engaged the instrument 20, but has just left its rest position. The "rest" (disengaged) position for the instrument driver 50 is one in which the end 56 of the driver 50 is disposed in the end wall 43 and out of the passage 46 so that the chamber 44 is free to rotate. In the position of FIG. 5, the hook 66 associated with the instrument 20 is preferably biased to a somewhat outward deflected position. In this regard, it is noted that the passage 46 has an enlarged section 46A that permits the hook 66 to deflect outwardly, as illustrated. The hooks are essentially spring biased outwardly so as to contact the inner wall surface of enlarged section 46A. This enables the driver to pass by the hooks 66 for engagement with the instrument 20.

As the driver 50 proceeds from the position illustrated in FIG. 5, toward the position illustrated in FIG. 6, the hook 64 passes under the hook 66 and as the driver is driven further to the left, as viewed in FIG. 3, the hooks 64 and 66 become interlocked in the position illustrated in FIG. 6 and there is thus cable continuity from cable 62 to cable 68. As is discussed in further detail hereinafter, the operation of these cables provide operation of certain actions of the end effector 18. As the driver end 56 engages the instrument end 25, the post 58 engages with the recess 26 so as to properly align the driver and instrument. At the initial point of contact the hooks 66 are still out of engagement with the hooks 64. However, as the driver moves further to the left the instrument starts to transition out of the storage chamber passage 46, and the hooks 66 transition into the smaller diameter section of the passage 46, causing them to deflect into engagement with the hooks 64, such as illustrated in FIG. 6. The coupling interface 59 formed essentially between the hooks 64 and 66 is maintained as the instrument transitions out of the instrument storage chamber 40. Refer to FIG. 7.

The driver 50 is of a sufficient length so that the selected instrument 20 is driven out of the chamber 44 and into the outlet guide tube 24. The instrument is then transitioned through the guide tube 24 to the position illustrated in FIG. 1 where the end effector or tool 18 of the instrument extends from the distal end of the guide tube 24 at a position inside the body cavity (operative site). All the while that the instrument is being transitioned to the end of the guide tube 24, the interconnecting cables are maintained in an interlocked position such as illustrated by the engaged hooks 64 and 66 in FIG. 6.

When it is desired to change to a different instrument, the driver 50 is withdrawn or in other words is moved in a direction to the right in FIG. 3. This carries the instrument with the instrument driver to the right and when the instrument reaches a position approximately as illustrated in FIG. 5, because of the increased diameter of the section 46A illustrated in FIG. 5, the hooks 66 are biased outwardly and disengage from the hooks 64. This essentially disengages the driver from the instrument and the driver is then in a position to be withdrawn through the port 49, no longer engaging with the instrument. This also leaves the instrument 20 in place in the instrument storage chamber 44 in readiness for a subsequent usage.

With the driver disengaged from the instrument, the instrument storage chamber can then be rotated to align a different instrument with the driver. The cabling in bundle 21, via base piece 51, controls the position of chamber 40 so as to select a different instrument by rotating the chamber 44 so that a different instrument registers with the driver 50. For an example of a registration mechanism refer to FIG. 14. A different instrument would also carry cabling similar to that illustrated in FIG. 5. Once the new instrument is in-line with the instrument driver 50 then the driver 50 may be engaged once again to pass through the port 49 engaging the new instrument and thus transitioning the new instrument out the outlet guide tube 24 to a position where the tool of the instrument is at the operative site in readiness for use and control from the master station surgeon interface.

A wide variety of different instruments may be supported in the instrument storage chamber 40. Tool 18 may include a variety of articulated tools, such as jaws, scissors, graspers, needle holders, micro dissectors, staple appliers, tackers, suction irrigation tools, clip appliers, that have end effectors driven by wire links, eccentric cams, push-rods or other mechanisms. In addition, tool 18 may comprise a non-articulated instrument, such as cutting blades, probes, irrigators, catheters or suction orifices. Alternatively, tool 18 may comprise an electrosurgical probe for ablating, resecting, cutting or coagulating tissue.

To provide proper alignment of the instrument 20 in the chamber 40 and with the driver 50 there are preferably provided interlocking surfaces such as a tongue and groove (not shown) between the walls of the chamber passage and the outer surface off the instrument and/or driver. Interlocking or guiding surfaces may also be provided within the guide tube 24. Thus, as the different instruments are moved in and out of the rotating chamber they will always be properly aligned with the driver so that the proper cabling is provided to control the instrument.

Reference is now made to FIG. 7 for a schematic illustration of the cabling as it extends from the bundle 22, through the driver 50, to the instrument 20, and the tool 18. The cabling extends about pulleys 29 and into the slots 61 in the instrument driver 50. FIG. 7 illustrates the driver 50 in a position in which it has entered the guide tube 24 and transitions to a location essentially at the end of the guide tube where the tool 18 is located and at the operative site OS. At the end of the driver where the cable hooks engage, such as illustrated in FIGS. 5 and 6, there is the coupling or interface section 59. FIG. 7 also illustrates the passages 46 and another non-selected tool within the instrument storage chamber.

Figure 8A:
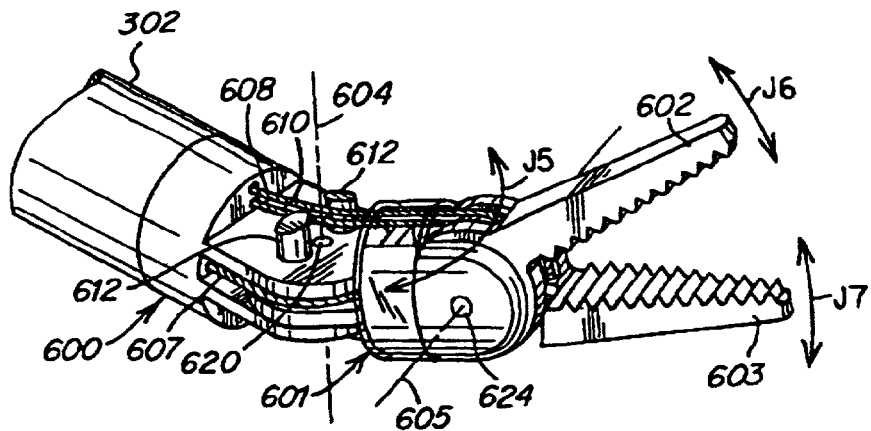
FIGS. 8A and 8B are perspective views of the tool component of the surgical instrument illustrating the cabling scheme.
Figure 8B:
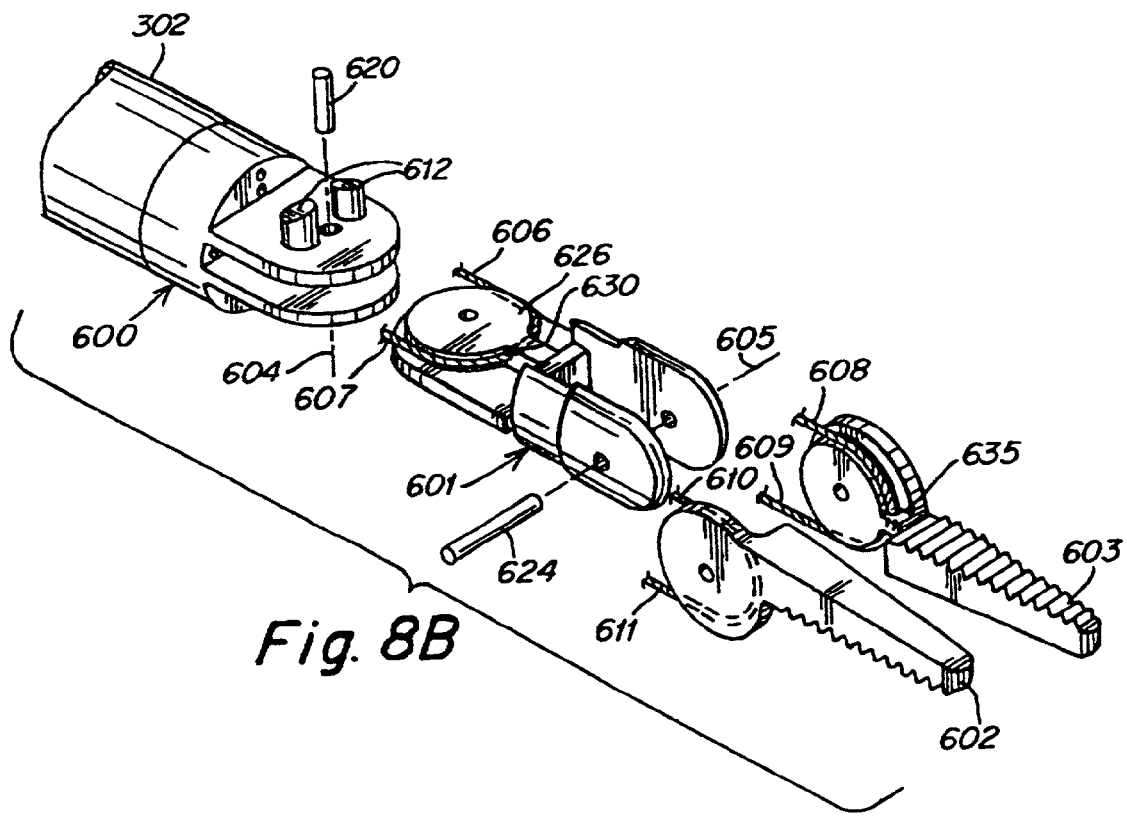
Figure 9:
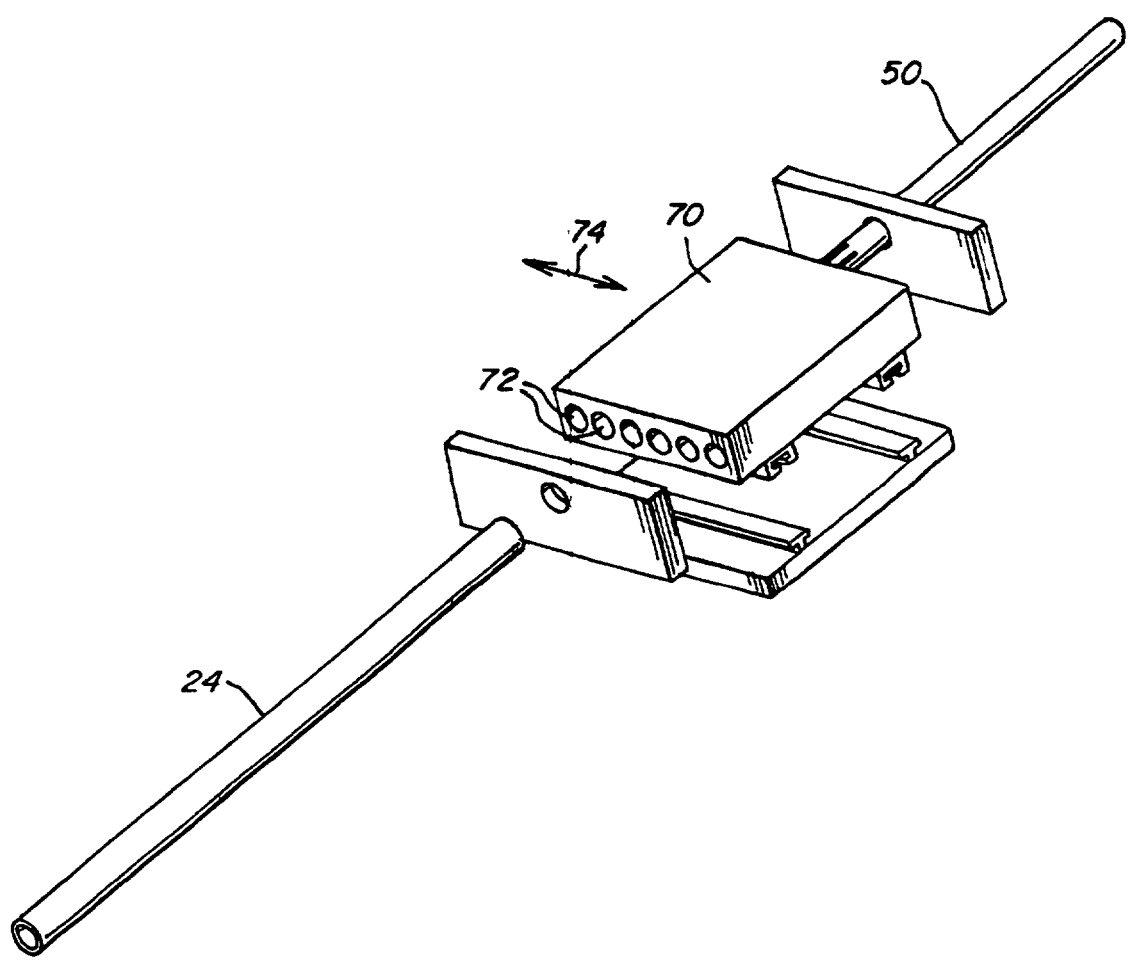
FIG. 9 is a perspective view of an alternate embodiment of the present invention, providing linear registration rather than rotational registration.

The construction of one form of tool is illustrated in FIGS. 8A and 8B. This is in the form of a set of jaws or grippers. This tool is shown for the purpose of illustration, it being understood that a variety of other tool may be used. FIG. 8A is a perspective view showing the tool pivoted at the wrist while FIG. 8B is an exploded view of the tool. The tool 18 is comprised of four members including the base 600, link 601, upper grip or jaw 602 and lower grip or jaw 603. The base 600 is affixed to the flexible stem section 302. This flexible section may be constructed of a ribbed plastic. This flexible section may be used when a curved end guide tube (see FIG. 11) is used so that the instrument will readily bend through the curved actuator tube 24.

The link 601 is rotatably connected to the base 600 about axis 604. FIG. 8B illustrates a pivot pin at 620. The upper and lower jaws 602 and 603 are rotatably connected to the link about axis 605, where axis 605 is essentially perpendicular to axis 604. FIG. 8B illustrates another pivot pin at 624.

Six cables 606-611, shown schematically in FIG. 8A and FIG. 8B, actuate the four members 600-603 of the tool. Cable 606 travels through the insert stem (section 302) and through a hole in the base 600, wraps around curved surface 626 on link 601, and then attaches on link 601 at 630. Tension on cable 606 rotates the link 601, and attached upper and lower grips 602 and 603, about axis 604( wrist pivot). Cable 607 provides the opposing action to cable 606, and goes through the same routing pathway, but on the opposite sides of the insert. Cable 607 may also attach to link 601 generally at 630. Cables 606 and 607 may be one continuous cable secured at 630.

Cables 608 and 610 also travel through the stem 302 and though holes in the base 600. The cables 608 and 610 then pass between two fixed posts 612. These posts constrain the cables to pass substantially through the axis 604, which defines rotation of the link 601. This construction essentially allows free rotation of the link 601 with minimal length changes in cables 608-611. In other words, the cables 608-611, which actuate the grips 602 and 623, are essentially decoupled from the motion of link 601. Cables 608 and 610 pass over rounded sections and terminate on grips 602 and 603, respectively. Tension on cables 608 and 610 rotate grips 602 and 603 counter-clockwise about axis 605. Finally, as shown in FIG. 8B, the cables 609 and 611 pass through the same routing pathway as cables 608 and 610, but on the opposite side of the instrument. These cables 609 and 611 provide the clockwise motion to grips or jaws 602 and 603, respectively. At the jaws 602 and 603, as depicted in FIG. 8B, the ends of cables 608-611 may be secured at 635. This securing may occur with the use of an adhesive such as an epoxy glue or the cables could be crimped to the jaw.

Reference is now made to FIG. 9. FIG. 9 schematically illustrated an alternate embodiment of the present invention. In FIGS. 1-8 the different instruments are selected by means of a rotating arrangement. In FIG. 9 the selection is made on an essentially linear basis. Thus, instead of the rotating member illustrated in FIGS. 1-8, there is a flat array 70 also having a series of elongated passages 72 extending therethrough. Each of these passages accommodates an instrument. FIG. 9 also schematically illustrates, by the same reference characters, the instrument driver 50 and the outlet guide tube 24 such as previously illustrated in FIGS. 1-8. The flat array 70 may be driven selectively in the direction of arrow 74 so as to align different ones of the passages 72 with the driver 50 and guide tube 24. Mechanisms for selective linear drive are well known, as are mechanisms for registration so as to provide proper alignment between the instrument and instrument driver.

In connection with the aforementioned description of the cables/hooks, it is noted that the interchange system is designed preferably to have all cabling maintained in tension. In this way, as an instrument is engaged, all of the cabling running therethrough is in tension and properly operative to control the end effector whether it be a set of jaws as illustrated in FIGS. 8A and 8B or some other type of instrument. If an end effector has less degrees of movement than that illustrated in FIGS. 8A and 8B this is still effectively controlled, but with the use of fewer cable control signals (fewer cables will actually be activated).

Reference is now made to the second robotic surgical system depicted in FIGS. 10-14, and that discloses a system having a greater number of degrees-of-freedom than the system described in FIGS. 1-8. In FIGS. 10-14 the same reference characters are used for similar components as depicted in FIGS. 1-8.

Figure 10:
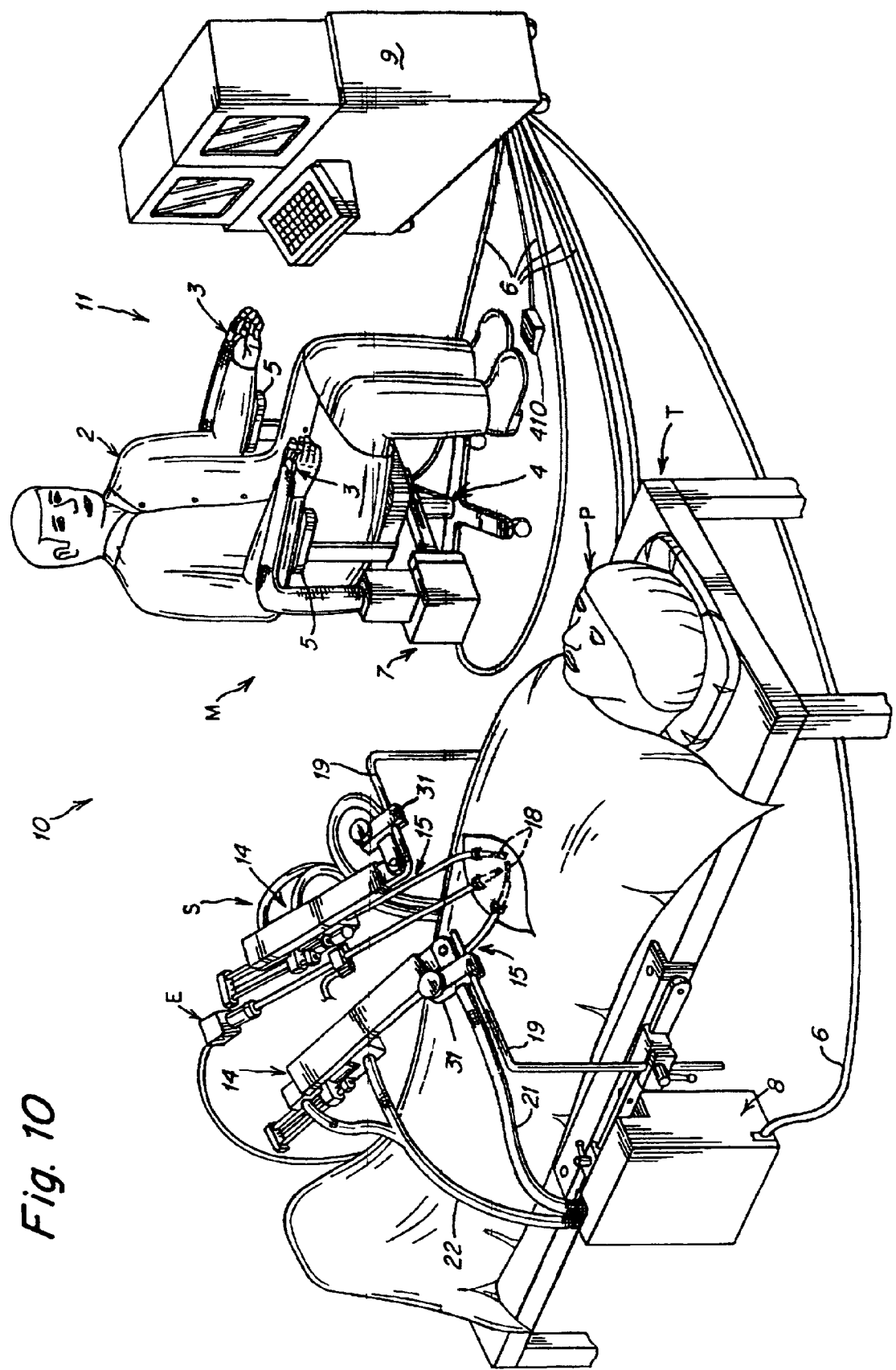
FIG. 10 is a perspective view of another embodiment of a robotic surgical system in which the interchangeable instrument principles of the present invention are applied.

The surgical robotic system, as illustrated in FIGS. 10-14, although preferably used to perform minimally invasive surgery, may also be used to perform other procedures as well, such as open or endoscopic surgical procedures. FIG. 10 illustrates a surgical instrument system 10 that includes a master station M at which a surgeon 2 manipulates an input device, and a slave station S at which is disposed a surgical instrument. In FIG. 1 the input device is illustrated at 3 being manipulated by the hand or hands of the surgeon. The surgeon is illustrated as seated in a comfortable chair 4. The forearms of the surgeon are typically resting upon armrests 5.

FIG. 10 illustrates a master assembly 7 associated with the master station M and a slave assembly 8 associated with the slave station S. Assembly 8 may also be referred to as a drive unit. Assemblies 7 and 8 are interconnected by means of cabling 6 with a controller 9. As illustrated in FIG. 10, controller 9 typically has associated therewith one or more displays and a keyboard. Reference is also made to, for example, the aforementioned U.S. Ser. No. 10/014,143, for further detailed descriptions of the robotic controller operation and associated algorithm.

As noted in FIG. 10, the drive unit 8 is remote from the operative site and is preferably positioned a distance away from the sterile field. The drive unit 8 is controlled by a computer system, part of the controller 9. The master station M may also be referred to as a user interface vis-à-vis the controller 9. Commands issued at the user interface are translated by the computer into an electronically driven motion in the drive unit 8. The surgical instrument, which is tethered to the drive unit through the cabling connections, produces the desired replicated motion. FIG. 10, of course, also illustrates an operating table T upon which the patient P is placed.

Thus, the controller couples between the master station M and the slave station S and is operated in accordance with a computer algorithm. The controller receives a command from the input device 3 and controls the movement of the surgical instrument so as to replicate the input manipulation.

With further reference to FIG. 10, associated with the patient P is the surgical instrument 14, which in the illustrated embodiment actually comprises two separate instruments one on either side of an endoscope E. The endoscope includes a camera to remotely view the operative site. The camera may be mounted on the distal end of the instrument insert, or may be positioned away from the site to provide additional perspective on the surgical operation. In certain situations, it may be desirable to provide the endoscope through an opening other than the one used by the surgical instrument 14. In this regard, in FIG. 10 three separate incisions are shown, two for accommodating the surgical instruments and a centrally disposed incision that accommodates the viewing endoscope. A drape is also shown with a single opening.

The surgical instrument 14 is generally comprised of two basic components including a surgical adaptor or guide 15 and an instrument 14. FIG. 10 illustrates the surgical adaptor 15, which is comprised primarily of the guide tube 24. In FIG. 10 the instrument 14 is not clearly illustrated but extends through the guide tube 24. The instrument 14 carries at its distal end the tool 18. Descriptions of the surgical instrument are found hereinafter in additional drawings, particularly FIG. 11. The surgical adaptor 15 is basically a passive mechanical device, driven by the attached cable array.

In FIG. 10 there is illustrated cabling 22 coupling from the instrument 14 to the drive unit 18. The cabling 22 is preferably detachable from the drive unit 8. Furthermore, the surgical adaptor 15 may be of relatively simple construction. It may thus be designed for particular surgical applications such as abdominal, cardiac, spinal, arthroscopic, sinus, neural, etc. As indicated previously, the instrument 14 couples to the adaptor 15 and essentially provides a means for exchanging the instrument tools. The tools may include, for example, forceps, scissors, needle drivers, electrocautery etc.

Referring still to FIG. 10, the surgical system 10 may preferably be used to perform minimally invasive procedures, although it is to be understood that the system may also be used to perform other procedures, such as open or endoscopic surgical procedures. The system 10 includes a surgeon's interface 11, computation system or controller 9, drive unit 8 and the surgical instrument 14. The surgical system 10, as mentioned previously, is comprised of an adaptor or guide 15 and the instrument 14. The system is used by positioning a tool 18 of the instrument, which is inserted through the surgical adaptor or guide 15. During use, a surgeon may manipulate the input device 3 at the surgeon's interface 11, to effect desired motion of the tool 18 within the patient. The movement of the handle or hand assembly at input device 3 is interpreted by the controller 9 to control the movement of the guide tube 24, instrument, and tool 18.

The surgical instrument 14, along with the guide tube 24 is mounted on a rigid post 19 which is illustrated in FIG. 10 as removably affixed to the surgical table T. This mounting arrangement permits the instrument to remain fixed relative to the patient even if the table is repositioned. Although, in FIG. 10 there are illustrated two such instruments, even a single surgical instrument may be used.

As indicated previously, connecting between the surgical instrument 14 and the drive unit 8, are cablings. These include two mechanical cable-in-conduit bundles 21 and 22.

These cable bundles 21 and 22 may terminate at two connection modules, not illustrated in FIG. 10 (see FIG. 1), which removably attach to the drive unit 8. Although two cable bundles are described here, it is to be understood that more or fewer cable bundles may be used. Also, the drive unit 8 is preferably located outside the sterile field, although it may be draped with a sterile barrier so that it may be operated within the sterile field.

In the preferred technique for setting up the system, and with reference to FIG. 10, the surgical instrument 14 is inserted into the patient through an incision or opening. The instrument 14 is then mounted to the rigid post 19 using a mounting bracket 31. The cable bundles 21 and 22 are then passed away from the operative area to the drive unit 8. The connection modules of the cable bundles are then engaged into the drive unit 8. The separate instrument members of instrument 14 are then selectively passed through the guide tube 24. This action is in accordance with the interchangeable instrument concepts of this invention.

The instrument 14 is controlled by the input device 3, which is be manipulated by the surgeon. Movement of the hand assembly produces proportional movement of the instrument 14 through the coordinating action of the controller 9. It is typical for the movement of a single hand control to control movement of a single instrument. However, FIG. 10 shows a second input device that is used to control an additional instrument. Accordingly, in FIG. 10 two input devices are illustrated and two corresponding instruments. These input devices are usually for left and right hand control by the surgeon.

The surgeon's interface 11 is in electrical communication with the controller 9. This electrical control is primarily by way of the cabling 6 illustrated in FIG. 10 coupling from the bottom of the master assembly 7. Cabling 6 also couples from the controller 9 to the actuation or drive unit 8. This cabling 6 is electrical cabling. The actuation or drive unit 8, however, is in mechanical communication with the instrument 14. The mechanical communication with the instrument 14 allows the electromechanical components to be removed from the operative region, and preferably from the sterile field. The surgical instrument 14 provides a number of independent motions, or degrees-of-freedom, to the tool 18. These degrees-of-freedom are provided by both the guide tube 24 and the instrument 14.

Figure 15:
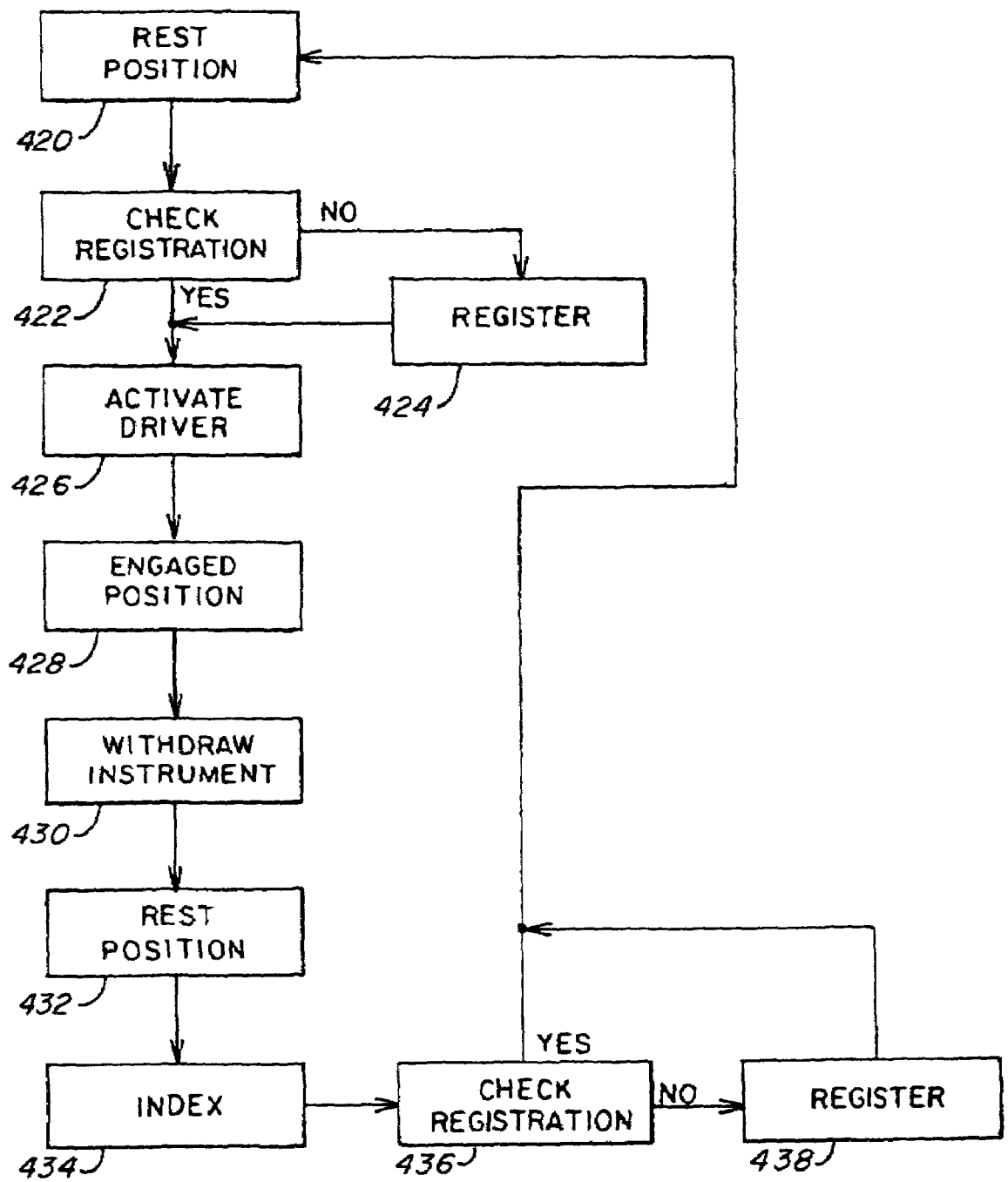
FIG. 15 is a block diagram illustrating the steps taken to provide indexing for instrument interchange.

FIG. 10 shows primarily the overall surgical system. FIGS. 11-14 show further details particularly of the interchangeable instrument concepts as applied to this system. FIG. 15 illustrates a control algorithm for the system. The system of FIG. 10 is adapted to provide seven degrees-of-freedom at the tool 18. Three of the degrees-of-freedom are provided by motions of the adaptor 15, while four degrees-of-freedom may be provided by motions of the instrument 14. As will be described in detail later, the adaptor is remotely controllable so that it pivots, translates linearly, and has its guide tube rotate. The instrument also rotates (through the instrument driver), pivots at its wrist, and has two jaw motions at the tool.

Now, reference is made to the more detailed drawings of FIGS. 11-14. FIG. 11 is a perspective view at the slave station of the system of FIG. 10 illustrating the interchangeable instrument concepts. FIG. 12 is a cross-sectional view through the storage chamber and as taken along line 12-12 of FIG. 11. FIG. 13 is a longitudinal cross-sectional view, as taken along line 13-13 of FIG. 11. FIG. 14 is a perspective schematic view of the indexing and registration mechanism used in the embodiment illustrated in FIGS. 10-13.

Reference is now made to FIG. 11 which is a perspective view illustrating the instrument 14 and the adaptor 15 at the slave station S. This instrument system is secured in the manner illustrated in FIG. 10 to the rigid post 19 that supports the surgical instrument by way of the mounting bracket 31 illustrated in FIG. 10, but not shown in FIG. 11. FIG. 11 also shows several cables that may be separated into five sets for controlling different motions and actions at the slave station. These are individual cables of the aforementioned bundles 21 and 22 referred to in FIG. 10. FIG. 11 also illustrates the support yoke 220 that is secured to the mounting bracket 31, the pivot piece 222, and support rails 224 for the carriage 226. The rails are supported in end pieces 241 and 262 with the end piece 241 attached to the pivot piece 222. The pivot piece 222 pivots relative to the support yoke 220 about pivot pin 225. A base piece 234 is supported under the carriage 226 by means of the support post 228. The support post 228 in essence supports the entire instrument assembly, including the adaptor 15 and the instrument 14.

As indicated previously, the support yoke 220 is supported in a fixed position from the mounting bracket 31. The support yoke 220 may be considered as having an upper leg 236 and a lower leg 238. In the opening 239 between these legs 236 and 238 is arranged the pivot piece 222. Cabling extends into the support yoke 220. This is illustrated in FIG. 11 by the cable set 501. Associated with the pivot piece 222 and the carriage 226 are pulleys (not shown) that receive the cabling for control of two degrees-of-freedom. This control from the cable set 501 includes pivoting of the entire instrument assembly about the pivot pin 225. This action pivots the guide tube 24 essentially in a single plane. This pivoting is preferably about an incision of the patient which is placed directly under, and in line with, the pivot pin 225. Other cables of set 501 control the carriage 226 in a linear path in the direction of the arrow 227. See also the cables 229 extending between the carriage 226 and the end pieces 241 and 262. The carriage moves the instrument and guide tube 24 back and forth in the direction of the operative site OS. Incidentally, in FIG. 11 the instrument is in its fully advanced state with the tool at the operative site OS.

The base piece 234 is the main support for the interchangeable instrument apparatus of the invention. Refer to FIGS. 11-14. The base piece 234 supports the guide tube 24, the instrument storage chamber 540, and the instrument driver 550. The instrument driver 550 is supported from another carriage, depicted in FIGS. 11 and 13 as the carriage 552, and that, in turn, is supported for translation on the carriage rails 554. The rails 554 are supported at opposite ends at end pieces 556 and 558, in a manner similar to the support for the other carriage 226. A support post 560 interconnects the carriage 552 with the instrument driver housing 570.

With further reference to FIG. 11, and as mentioned previously, there are a number of cable sets from bundles 21 and 22 coupled to and for controlling certain actions of the instrument system. Mention has been made of the cable set 501 for controlling instrument pivoting and translation, as previously explained. In addition, FIG. 11 depicts four other cable sets 503, 505, 507, and 509. Cable set 503 controls rotation of the guide tube 24. Cable set 505 controls the carriage 552, and, in turn, the extending and retracting of the instrument driver for instrument exchange. Cable set 507 controls rotation of the instrument through rotation of the instrument driver. Finally, cable set 509 controls the tool via the instrument driver and instrument. There is also one other set of control cables not specifically illustrated in FIG. 11 that controls the indexing motor 565, to be discussed in further detail later.

FIG. 13 shows a cross-sectional view through the interchangeable instrument portion of the overall instrument system. This clearly illustrates the internal cable and pulley arrangement for the various motion controls. There is a pulley 301 driven from the cable set 503 that controls rotation of the guide tube 24. There is also a pulley 303 driven from cable set 505, along with a companion pulley 305 that provides control for the carriage 552. FIG. 13 also illustrates another pulley 307 driven from cable set 507, and for controlling the rotation of the instrument driver 550, and, in turn, the selected instrument.

FIG. 13 illustrates the guide tube 24 supported from the base piece 234. The guide tube 24 is hollow and is adapted to receive the individual instruments or work sections 541 disposed in the instrument storage chamber 540, as well as the instrument driver 550. Refer to FIG. 7 for an illustration of the instrument and instrument driver positioned in the guide tube 24. FIG. 13 shows the instrument driver 550 in its rest or disengaged position. The proximal end 24A of the guide tube 24 is supported in the base piece 234 by means of a pair of bearings 235 so that the guide tube 24 is free to rotate in the base piece 234. This rotation is controlled from the pulley 237 which is secured to the outer surface of the guide tube 24 by means of a set screw 231. The pulley 237 is controlled to rotate by means of the cabling 310 that intercouples the pulleys 301 and 237 and that is an extension of the cabling 503. Thus, by means of the cable and pulley arrangement, and by means of the rotational support of the guide tube 24, the rotational position of the guide tube 24 is controlled from cable set 503. Of course, this controlled rotation is effected from the master station via the controller 9, as depicted in the system view of FIG. 10, and as a function of the movements made by the surgeon at the user interface 11.

As indicated before the proximal end 24A of the guide tube 24 is supported from the base piece 234. The distal end of the guide tube 24, which is adapted to extend through the patient incision, and is disposed at the operative site OS illustrated about the tool 18 in FIG. 11, and where a medical or surgical procedure is to be performed. In the system shown in FIG. 11 the distal end of the guide tube 24 is curved at 24B. In this way by rotating the guide tube 24 about its longitudinal axis there is provided a further degree-of-freedom so as to place the end tool at any position in three-dimensional space. The rotation of the guide tube 24 enables an orbiting of the end tool about the axis of the guide tube 24. The guide tube 24 is preferably rigid and constructed of a metal such as aluminum. The tool 18 illustrated in FIG. 11 may be the same tool as illustrated in FIGS. 8A and 8B. Also, when the instrument is fully engaged, as in FIG. 11, the cabling and cable interface is as illustrated in FIG. 7.

FIG. 13 also illustrates a cross-section of the instrument storage chamber 540 including the storage magazine 549, and showing two of the six instrument passages 542 in the storage magazine 549. The instrument storage chamber may also be referred to herein as an instrument retainer. In FIG. 13 one of the instruments 541 is about to be engaged by the instrument driver 550. The other instrument 541 is in place (storage or rest position) in the instrument storage chamber 540, and out of the path of the instrument driver 550. One of the instruments 541 carries a gripper tool illustrated at 543, while the other instrument carries a scissors 544. Because these instruments are adapted to pass to the guide tube 24 and be positioned at the distal end 24B thereof, the body 548 of the instrument is flexible so as to be able to curve with the curvature of the guide tube 24.

Although reference is made herein to the separate instrument and instrument driver, such as illustrated in FIG. 13, once they are engaged they function as a single piece instrument member. Accordingly reference is also made herein to the instrument driver 550 as a "driver section" of the overall one piece instrument member, and the instrument 541 as a "working" section of the instrument member. The instrument member has also been previously discussed as having a "coupling section" or "interface section", which is defined between the working section and the driver section where the cables interlock by means of the engaging hook arrangement, such as clearly depicted in FIGS. 5 and 6. This is shown in FIG. 13 at 559. This is analogous to the interface 59 illustrated in FIG. 7.

The carriage 552 illustrated in FIG. 13 is moved linearly by the cables 555 that extend between pulleys 303 and 305. These cables attach to the carriage 552. The carriage movement is controlled from cable set 505. It is the movement of the carriage 552 that drives the instrument driver(driver section) 550. The instrument driver 550, in its rest or disengaged position, is supported between the instrument driver housing 570 and the wall 562 that is used for support of the instrument storage chamber 540. The instrument magazine 549 is rotationally supported by means of the axle or shaft 547, with the use of bushings or bearings, not shown. This support is between walls 562 and 563.

FIG. 13 shows the very distal end 525 of the instrument driver (transporter) 550 supported at wall 562. In the rest position of the instrument driver 550 the driver is out of engagement with the instruments and the magazine 549, thus permitting rotation of the instrument storage chamber 540. The proximal end 526 of the instrument driver 550 is supported at the instrument driver housing 570. It may be rotationally supported by means of a bushing 527. The instrument driver 550 is supported for rotation, but rotation is only enabled once the driver has engaged the instrument and preferably is at the operative site. The rotation of the instrument driver 550 is controlled from cable set 503 by way of the pulley 307.

In FIG. 11 the cable set 509 is illustrated as controlling the instrument motions including tool actuation. These cables control a series of pulleys shown in FIG. 13 as pulleys 529. As indicted in FIG. 13 these pulleys control cabling that extends through the instrument driver and the instrument for control of instrument and tool motions. The cables that are controlled from these pulleys may control three degrees-of-freedom of the instrument, including pivoting at the wrist and two for gripper action. For the details of the interlocking of the instrument and instrument driver refer to FIGS. 5 and 6. The same engagement arrangement can be used in this second embodiment of the invention including the mating hook arrangement, interlocked at interface 559 when the instrument driver and instrument are engaged.

Reference has been made before to the indexing motor 565. This motor is illustrated in FIG. 11 positioned next to the base piece 234, and is further illustrated in FIG. 14 located for interaction with the instrument storage chamber 540. The indexing motor 565 is controlled from the master station side, and accordingly there is another cable set (not shown) that actuates the indexing motor 565. The indexing motor 565 may be a stepper motor having a degree of rotation that corresponds to the desired rotation of the instrument storage chamber 540. The stepper motor may be designed to provide 60 degrees of rotation for each actuation, corresponding to an instrument storage chamber 540 having six passages (360 degrees divided by 6) for receiving instruments.

In FIG. 14 the stepper motor 565 has an output shaft 566 that supports an indexing disk 567, shown also in dashed line in FIG. 12. The indexing disk 567 is fixed to the shaft 566 and so rotates with the shaft 566. FIG. 12 illustrates the disk 567 carrying four pins 568 disposed at the periphery of the disk 567. FIG. 14 also shows these pins 568. The pins 568 selectively engage in indexing slots 569 in an end wall of the magazine 549. To insure that the rotating chamber stays in proper registration with the instrument driver a spring and ball detent arrangement is employed. Refer to FIGS. 11-14 illustrating a standard ball and spring member 575 supported in the wall 563. The ball of member 575 is urged against an end wall surface 576 of the magazine 549. This end wall has a series of detent dimples 577 (see FIG. 14) disposed at locations corresponding to the passages in the magazine 549. The stepper motor 565 is selectively operated under surgeon control from the master station. Each step rotates the disk 567 through 90 degrees. The engagement of the pins 568 with the slots 569 causes a corresponding rotation of the magazine 549 through 60 degrees. Each subsequent rotation of the stepper motor 565 causes a further 60 degree rotation of the magazine 549. The stepper motor 565 is controllable in a manner so that, with proper decoding, there may be multiple step actuations to get from one instrument to the next selected instrument.

The operation of the slave instrument is in a robotic manner from the master station, such as illustrated in FIG. 10. The surgeon can control several degrees-of-freedom of the instrument system. In addition, when the surgeon wishes to exchange instruments this can be done directly from the master station from an actuation member and at the proper time in the surgical procedure. One type of actuation member may be by means of a foot switch 410 illustrated in FIG. 10 within access of the surgeon. The foot switch 410 couples to the controller 9. Appropriate electrical signals are coupled from the master station to the slave station basically to control the stepper motor 565 for indexing the magazine 549.

The sequence of operation for the indexing is demonstrated in the flow chart of FIG. 15. This block diagram indicates the sequence of steps performed commencing with a rest position of the system in which the instruments are all in place in the storage chamber 540, and the instrument driver is in the position substantially as illustrated in FIG. 13, just out of contact with the registered instrument and with the driver end 525 disposed in the wall 562. It is this position that is illustrated in FIG. 15 by box 420. The next step is to check the registration of the instrument driver with the instrument itself. This is depicted by the box 422. This step may involve the use of some known registration system, such as one using an optical sensing arrangement to determine proper registration between the instrument driver 550 and each of the passages in the magazine 549, along with the instrument 541. If proper registration is detected then the system proceeds to the next step indicated in FIG. 15 by box 426, which activates the instrument driver 550. This starts the process of driving the instrument to the operative site OS. This involves mechanical control signals on the cable set 505 controlling the carriage 552, and in turn, the instrument driver 550. If an improper registration is detected then box 424 indicates the step of correcting the registration. This may be carried out in a well known manner with the use of an optical system to provide slight rotation to the instrument storage chamber 540 so as to obtain proper registration. This system may also use some type of a feedback system.

The next step in the system is indicated in FIG. 15 by the box 428 which simply detects the fully engaged position of the instrument driver and instrument. This is the position illustrated in FIG. 11. Again, this position can be readily detected by optical means. The next step illustrated in FIG. 15 by box 430 is one that commences the interchange process. The intercoupled instrument and instrument driver are withdrawn. This involved movement of the carriage 552 in the opposite direction. Next, indicated by box 432, is where the instrument and instrument driver have reached the position illustrated in FIG. 13 previously referred to as the "rest position". In that position the instrument driver (transporter) 550 is clear of the instrument storage chamber 540, and thus the instrument storage chamber 540 can be indexed (rotated). This is shown in FIG. 15 by the box 434. Following these steps, from FIG. 15 it is seen that there may be another registration check (box 436), and a correction (box 438), in a manner similar to the operation previously discussed regarding boxes 422 and 424. The process can then repeat at a time determined by the surgeon's instrument selection sequence.

There has to be some correlation between the indexing, what and where particular instruments are stored, and how the indexing is controlled from the master station. As indicated previously a foot switch can be used, such as the switch 410 illustrated in FIG. 10. In one version of the control the switch 410 may be comprised of six separate actuation buttons, each one corresponding to one of the six instruments disposed in the instrument storage chamber 540. Indicia may be provided associated with the storage chamber to indicate what particular instrument is disposed in what particular instrument passage. In this way the surgeon would know what button to actuate to select the desired instrument. There could be corresponding indicia associated with the switch buttons so the surgeon knows what button corresponds exactly to what instrument.

The control system for indexing may also include a decoding scheme so that when the surgeon makes a selection the decoder determines the number of rotations (such as of the stepper motor 565) necessary to bring the instrument driver into proper registration with the selected instrument. Because it may not always be clear as to the specific instrument sequence that the surgeon will use, the system has to determine how to index from one instrument to the next one selected. This selection process involves more than just sequencing from one instrument to an adjacent instrument. The process will have to accommodate a selection process in which the next selected instrument is not the adjacent instrument. Thus a simple decoder can be used to determine the number of stepper motor steps necessary to move the storage chamber to the next selected instrument.

Another aid that can be provided to the surgeon is a visible display illustrated in FIG. 10, and on which there can be a diagram that matches the storage chamber pattern showing to the surgeon exactly where each instrument is placed including the type of instrument. This could be set up when the instruments are first selected the disposed in the instrument storage chamber 540. In association with this display one could also provide, in place of the switch 410, a voice activated system so that the surgeon simply indices by voice which instrument to select. This may be done by simply numbering the instruments, such as one through six. A further variation may use a touch screen so that the surgeon simply touches an area on the screen corresponding to the displayed image of the storage chamber with the stored instruments. In all of the above instances, there are electrical signals generated from the master station, through a touch screen, switch, etc. that are conveyed to the controller 9 and from there to the slave side. The activating signals at the slave side basically control the stepper motor 565 via a cable set not specifically shown in the drawings but that would couple to the stepper motor 565 illustrated in FIGS. 11, 12 and 14.

Figure 16:
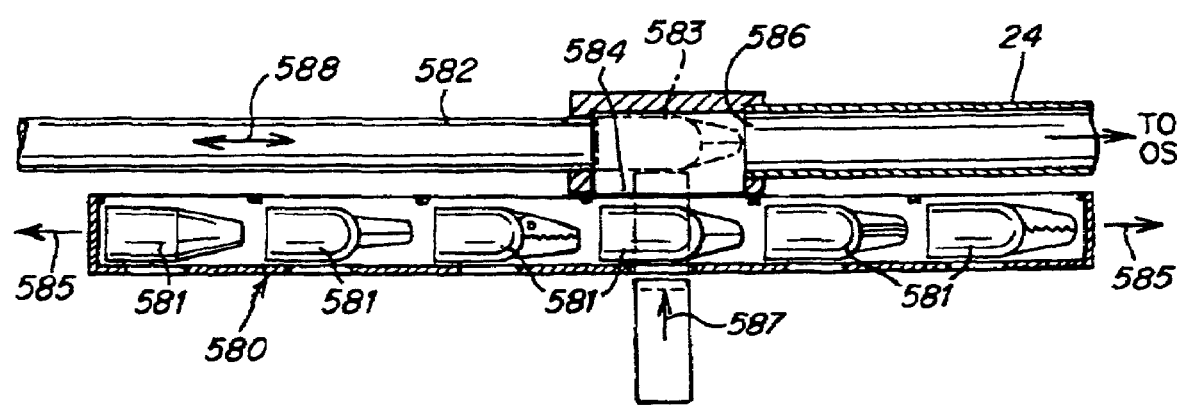
FIG. 16 is a schematic diagram of another alternate embodiment of the invention using a serial storage concept.

Reference is now made to FIG. 16 for a schematic representation of a further alternate embodiment of the invention. In FIGS. 1 and 10 it is noted that the instruments are contained in a parallel array. In accordance with the invention the instruments may also be disposed in a series array, as depicted in the schematic diagram of FIG. 16. This embodiment includes a retainer 580 that is adapted to store a series of instruments 581 in a serial array, also referred to herein as a linear chamber or linear retainer. Means are provided to enable the array to move laterally in the directions indicated by arrows 585. This movement can be of either the retainer or the instruments themselves. There is an alignment that occurs so that a selected instrument may align with a port 584 from which the instrument may then be moved to location 583. This is by a lateral or transverse movement of the instrument out of the retainer 580. This movement is indicated in FIG. 16 by the arrow 587. The instrument, once moved, is then in registration with the driver or transporter 580 which is moveable in the direction of arrow 588. The driver is controlled as in previous embodiments to transition the instrument to the operative site, through the represented output port 586.

Although reference is made herein to "surgical instrument" it is contemplated that the principles of this invention also apply to other medical instruments, not necessarily for surgery, and including, but not limited to, such other implements as catheters, as well as diagnostic and therapeutic instruments and implements.

Having now described certain embodiments of the present invention, it should be apparent to one skilled in the art that numerous other embodiments and modifications thereof can be made, some of which have already been described, and all of which are intended to fall within the scope of the present invention. For example, the coupling sections or interface sections have been disclosed as intercoupled cables with hook arrangements, such as shown in FIG. 6. In another arrangement a different mechanical coupling scheme may be employed using a different interlock between cables. Also, in place of mechanical couplings other technologies may be used for coupling action to the instrument and tool, such as SMA technology. Regarding the tool itself, one has been illustrated with a wrist pivot. Instead the tool may include a bendable section at or near its distal end. In place of the stepper motor other indexing arrangements can be used, such as a ratchet and pawl system. Also, encoders can be used at the rotating storage chamber to detect motions to provide feedback for controlling the overall system.

What is claimed is:

1. An interchangeable instrument system, comprising:
a plurality of separate instrument members each capable of assisting in a different phase of a medical procedure to be performed at an anatomical operative site;
a single instrument storage chamber for releasably receiving said instrument members accommodated in separate storage locations within said instrument storage chamber;
an instrument driver constructed and arranged for cooperative positioning relative to said instrument storage chamber, for selective coaxial alignment with one of said instrument members at a time, and for displacing said aligned instrument member from said instrument storage chamber toward said operative site; and
an indexing mechanism for positionally controlling at least one of said instrument driver and instrument storage chamber so as to provide relative displacement therebetween, whereby said indexing mechanism selectively and coaxially aligns said instrument driver with different ones of said instrument members.

2. A system as set forth in claim 1 wherein said instrument storage chamber comprises a rotating chamber having said storage locations therein.

3. A system as set forth in claim 2 wherein each of said instrument members has a rest storage position when disposed in the instrument storage chamber, and a working position when coupled to said operative site, and further comprising an outlet guide tube for receiving said aligned instrument member when said aligned instrument member is in its working position.

4. A system as set forth in claim 3 wherein said indexing mechanism is for rotating said instrument storage chamber so that said different ones of said instrument members may be coaxially aligned with said outlet guide tube.

5. A system as set forth in claim 4 further comprising a carriage for supporting and linearly translating said instrument driver.

6. A system as set forth in claim 1 wherein said instrument driver has cabling and said one instrument member has cabling.

7. A system as set forth in claim 6 further including a coupling interface for selectively connecting said cabling of said instrument driver with said cabling of said one instrument member.

8. A system as set forth in claim 7 wherein said coupling interface comprises corresponding hooks associated with said instrument driver and said one instrument member, and engageable when said instrument driver selects said one instrument member.

9. A system as set forth in claim 5 further comprising a base piece for supporting said carriage for rotation about a central axis.

10. A system as set forth in claim 8 wherein each storage location in the said instrument storage chamber has an enlarged section to facilitate disengagement of said engageable hooks.

11. A system as set forth in claim 10 wherein facing ends of said instrument driver and said one instrument member have interlocking surfaces.

12. A system as set forth in claim 1 further comprising a drive unit for operating a tool at a distal end of each of said instrument members.

13. A system as set forth in claim 12 wherein said drive unit is configured to be remotely controlled from a user interface.

14. A system as set forth in claim 1 wherein said indexing mechanism is for controlling the position of said instrument storage chamber.

15. A system as set forth in claim 13 further comprising an actuation member at said user interface for remotely controlling said indexing mechanism.

16. A system as set forth in claim 15 wherein said actuation member includes at least one of a switch, touch screen, pointer, or voice activation device.

17. An interchangeable instrument system, comprising:
a single storage retainer that supports a plurality of separately arranged instruments, and includes inlet and outlet ports, said outlet port configured to be arranged in coaxial alignment with a target or operative site where a selected one of said instruments is to be delivered for performing a medical procedure, said storage retainer being selectively operable, upon command, to permit different instruments to coaxially align between said inlet and outlet ports;

a work implement supported at the distal end of each instrument; and an instrument transporter in coaxial alignment with said inlet port, and adapted to engage said selected instrument disposed in said storage retainer, so as to deliver said selected instrument, via said outlet port to said target or operative site, said instrument transporter, in addition to engagement with said selected instrument, also operatively coupling with and enabling operation of said work implement of said selected instrument.

18. A system as set forth in claim 17 further comprising an electrical controller for operating said work implement of said selected instrument in response to a remote user interface.

19. A system as set forth in claim 18 wherein said storage retainer further includes an instrument storage chamber and an indexing mechanism for controlling the position of said instrument storage chamber.

20. A system as set forth in claim 19 further comprising an actuation member at said user interface for remotely controlling said indexing mechanism.

21. A system as set forth in claim 20 wherein said actuation member includes at least one of a switch, touch screen, pointer, or voice activation device.

22. An interchangeable instrument system, comprising:

a single instrument retainer having multiple storage locations for receiving a plurality of instruments disposed separately in said respective storage locations;

an instrument driver constructed and arranged for cooperative positioning relative to said instrument retainer, for selective coaxial alignment with one of said instruments at a time, and for displacing said aligned instrument from said instrument retainer toward an anatomical operative site;

an indexing mechanism controlling the position of said instrument retainer, whereby said indexing mechanism selectively and coaxially aligns different ones of said instruments with said instrument driver; and an actuation member disposed at a user interface for controlling said indexing mechanism.

23. A system as set forth in claim 22 further comprising an electrical controller for operating said indexing mechanism in response to command signals from said user interface.

24. A system as set forth in claim 22 wherein said actuation member includes at least one of a switch, touch screen, pointer, or voice activation device.

25. A system as set forth in claim 22 wherein said user interface is a remote user interface.

26. An interchangeable instrument system, comprising:

a plurality of medical instruments;

a single instrument retainer for releasably holding said instruments; and an instrument transporter associated with said instrument retainer, for selective coaxial alignment with one of said instruments at a time, and for displacing said aligned instrument from said instrument retainer toward an anatomical operative site; and an indexing mechanism for positionally controlling at least one of said instrument retainer and instrument transporter so as to provide relative displacement therebetween, whereby said indexing mechanism selectively and coaxially aligns said instrument transporter with different ones of said instruments.

27. An interchangeable instrument system as set forth in claim 26 further comprising a driver for controlling said indexing mechanism in response to command signals from a remote user interface.

28. An interchangeable instrument system as set forth in claim 27 further comprising an actuation member disposed at said remote user interface for controlling said indexing mechanism.

29. An interchangeable instrument system as set forth in claim 26 wherein said instrument retainer comprises a rotating chamber having a plurality of passages therein.

30. An interchangeable instrument system as set forth in claim 26 wherein said instrument retainer comprises a linear chamber for receiving said instruments.

31. An interchangeable instrument system as set forth in claim 30 wherein said instrument transporter is positioned in parallel to said linear chamber, and a selected instrument is configured to be moved transversely out of said chamber for coaxial alignment with said instrument transporter.

32. An interchangeable instrument system as set forth in claim 26 wherein said indexing mechanism is for controlling the position of said instrument retainer so as to selectively coaxially align said different ones of said instruments with said instrument transporter.

* * * * *